United States Patent
el Kaliouby et al.

(10) Patent No.: US 11,410,438 B2
(45) Date of Patent: Aug. 9, 2022

(54) IMAGE ANALYSIS USING A SEMICONDUCTOR PROCESSOR FOR FACIAL EVALUATION IN VEHICLES

(71) Applicant: Affectiva, Inc., Boston, MA (US)

(72) Inventors: Rana el Kaliouby, Milton, MA (US); Abdelrahman N. Mahmoud, Somerville, MA (US); Taniya Mishra, New York, NY (US); Boisy G. Pitre, Opelousas, LA (US); Panu James Turcot, Pacifica, CA (US); Andrew Todd Zeilman, Beverly, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 16/678,180

(22) Filed: Nov. 8, 2019

(65) Prior Publication Data
US 2020/0074154 A1    Mar. 5, 2020

Related U.S. Application Data

(63) Continuation-in-part of application No. 16/429,022, filed on Jun. 2, 2019, which is a continuation-in-part
(Continued)

(51) Int. Cl.
*G06V 20/59* (2022.01)
*G16H 30/40* (2018.01)
(Continued)

(52) U.S. Cl.
CPC ............ *G06V 20/597* (2022.01); *A61B 5/165* (2013.01); *A61B 5/18* (2013.01); *A61B 5/6898* (2013.01);
(Continued)

(58) Field of Classification Search
CPC .......... G06K 9/00845; G06K 9/00302; G06K 9/00288; G06K 9/00281; B60K 28/02;
(Continued)

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 | |
| JP | 2005316704 A | * 11/2005 | ............... G06T 1/00 |

(Continued)

OTHER PUBLICATIONS

Fasel, B. (2002, August). Robust face analysis using convolutional neural networks. In Object recognition supported by user interaction for service robots (vol. 2, pp. 40-43). IEEE.
(Continued)

*Primary Examiner* — Casey L Kretzer
(74) *Attorney, Agent, or Firm* — Adams Intellex, PLC

(57) ABSTRACT

Analysis for convolutional processing is performed using logic encoded in a semiconductor processor. The semiconductor chip evaluates pixels within an image of a person in a vehicle, where the analysis identifies a facial portion of the person. The facial portion of the person can include facial landmarks or regions. The semiconductor chip identifies one or more facial expressions based on the facial portion. The facial expressions can include a smile, frown, smirk, or grimace. The semiconductor chip classifies the one or more facial expressions for cognitive response content. The semiconductor chip evaluates the cognitive response content to produce cognitive state information for the person. The semiconductor chip enables manipulation of the vehicle
(Continued)

based on communication of the cognitive state information to a component of the vehicle.

28 Claims, 20 Drawing Sheets

Related U.S. Application Data of application No. 15/875,644, filed on Jan. 19, 2018, now Pat. No. 10,627,817, which is a continuation-in-part of application No. 15/273,765, filed on Sep. 23, 2016, now abandoned, application No. 16/678,180, which is a continuation-in-part of application No. 14/947,789, filed on Nov. 20, 2015, now Pat. No. 10,474,875, said application No. 15/273,765 is a continuation-in-part of application No. 14/796,419, filed on Jul. 10, 2015, now abandoned, which is a continuation-in-part of application No. 14/460,915, filed on Aug. 15, 2014, now abandoned, said application No. 14/947,749 is a continuation-in-part of application No. 14/460,915, said application No. 14/947,749 is a continuation-in-part of application No. 13/708,027, filed on Dec. 7, 2012, now abandoned, which is a continuation-in-part of application No. 13/153,745, filed on Jun. 6, 2011, now abandoned, said application No. 14/460,915 is a continuation-in-part of application No. 13/153,745.

(60) Provisional application No. 62/926,009, filed on Oct. 25, 2019, provisional application No. 62/925,990, filed on Oct. 25, 2019, provisional application No. 62/893,298, filed on Aug. 29, 2019, provisional application No. 62/827,088, filed on Mar. 31, 2019, provisional application No. 62/679,825, filed on Jun. 3, 2018, provisional application No. 62/611,780, filed on Dec. 29, 2017, provisional application No. 62/593,449, filed on Dec. 1, 2017, provisional application No. 62/593,440, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/217,872, filed on Sep. 12, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/581,913, filed on Dec. 30, 2011, provisional application No. 61/568,130, filed on Dec. 7, 2011, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.
| | | |
|---|---|---|
| *A61B 5/18* | | (2006.01) |
| *A61B 5/00* | | (2006.01) |
| *A61B 5/16* | | (2006.01) |
| *B60K 28/02* | | (2006.01) |
| *G06V 40/16* | | (2022.01) |

(52) U.S. Cl.
CPC ............ *A61B 5/7267* (2013.01); *B60K 28/02* (2013.01); *G06V 40/162* (2022.01); *G06V 40/171* (2022.01); *G06V 40/172* (2022.01); *G06V 40/174* (2022.01); *G16H 30/40* (2018.01)

(58) Field of Classification Search
CPC ......... A61B 5/18; A61B 5/165; A61B 5/7267; A61B 5/6898; G06V 20/597; G06V 40/162; G06V 40/171; G06V 40/172; G06V 40/174; G16H 30/40
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |

(56) References Cited

U.S. PATENT DOCUMENTS

| | | |
|---|---|---|
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,154,723 A * | 11/2000 | Cox ................. G06F 3/011 345/419 |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 6,927,694 B1 | 8/2005 | Smith et al. |
| 7,003,135 B2 | 2/2006 | Hsieh et al. |
| 7,013,478 B1 | 3/2006 | Hendricks et al. |
| 7,027,621 B1 | 4/2006 | Prokoski |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,947,217 B2 | 2/2015 | Moussa et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0011399 A1 | 1/2006 | Brockway et al. |
| 2006/0019224 A1 | 1/2006 | Behar et al. |
| 2006/0115157 A1 | 6/2006 | Mori et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0104362 A1 * | 5/2007 | Hwang ............. G06K 9/00275 382/159 |
| 2007/0167689 A1 | 7/2007 | Ramadas et al. |
| 2007/0173733 A1 | 7/2007 | Le et al. |
| 2007/0183635 A1 * | 8/2007 | Weidhaas ......... G06K 9/00228 382/118 |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0167757 A1 * | 7/2008 | Kanevsky ............. G07C 5/085 701/1 |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2008/0294012 A1 * | 11/2008 | Kurtz .................... A61B 5/445 600/300 |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0129638 A1 * | 5/2009 | Kim .................. G06K 9/00295 382/118 |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0244323 A1 * | 10/2009 | Carter ................ H04N 5/23293 348/231.99 |
| 2009/0259518 A1 | 10/2009 | Harvey |
| 2009/0270170 A1 | 10/2009 | Patton |
| 2009/0271417 A1 | 10/2009 | Toebes et al. |

(56) References Cited

U.S. PATENT DOCUMENTS

| | | |
|---|---|---|
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0134302 A1* | 6/2010 | Ahn .................. A61B 5/18 340/576 |
| 2010/0266213 A1 | 10/2010 | Hill |
| 2010/0274847 A1 | 10/2010 | Anderson et al. |
| 2010/0296706 A1 | 11/2010 | Kaneda et al. |
| 2010/0324437 A1 | 12/2010 | Freeman |
| 2011/0032378 A1* | 2/2011 | Kaneda .............. G06K 9/00248 348/222.1 |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0109452 A1 | 5/2012 | Autran et al. |
| 2012/0150430 A1 | 6/2012 | French et al. |
| 2012/0209634 A1* | 8/2012 | Ling .................. G06Q 10/0833 705/4 |
| 2012/0271484 A1* | 10/2012 | Feit ...................... B60W 10/18 701/1 |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2014/0171752 A1 | 6/2014 | Park et al. |
| 2014/0172910 A1 | 6/2014 | Jung et al. |
| 2014/0218187 A1 | 8/2014 | Chun et al. |
| 2015/0098634 A1* | 4/2015 | Ohsuga .............. G06K 9/00261 382/118 |
| 2015/0258995 A1 | 9/2015 | Essers et al. |
| 2016/0104486 A1 | 4/2016 | Penilla et al. |
| 2016/0379486 A1* | 12/2016 | Taylor ................ G01C 21/3691 340/905 |
| 2017/0003784 A1 | 1/2017 | Garg et al. |
| 2019/0176837 A1 | 6/2019 | Williams et al. |

FOREIGN PATENT DOCUMENTS

| | | |
|---|---|---|
| KR | 10-2005-0021759 A | 3/2005 |
| KR | 10-2008-0016303 A | 2/2008 |
| KR | 1020100048688 A | 5/2010 |
| WO | 2011/045422 A1 | 4/2011 |

OTHER PUBLICATIONS

Matsugu, M., Mori, K., Mitari, Y., & Kaneda, Y. (2003). Subject independent facial expression recognition with robust face detection using a convolutional neural network. Neural Networks, 16(5-6), 555-559.

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al., Learning and Incorporating Top-Down Cues in Image Segmentation, 2006, Lecture Notes in Computer Science, ISBN 978-3-540-33832-1, Springer-Verlag, Germany.

Ross Eaton, et al., Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

* cited by examiner

IMAGE ANALYSIS USING A SEMICONDUCTOR PROCESSOR FOR FACIAL EVALUATION IN VEHICLES

RELATED APPLICATIONS

This application claims the benefit of U.S. provisional patent applications "Image Analysis for Human Perception Artificial Intelligence" Ser. No. 62/827,088, filed Mar. 31, 2019, "Vehicle Interior Object Management" Ser. No. 62/893,298, filed Aug. 29, 2019, "Deep Learning In Situ Retraining" Ser. No. 62/925,990, filed Oct. 25, 2019, and "Data Versioning for Neural Network Training" Ser. No. 62/926,009, filed Oct. 25, 2019.

This application is also a continuation-in-part of "Image Analysis Using a Semiconductor Processor for Facial Evaluation" Ser. No. 14/947,789, filed Nov. 20, 2015, which claims the benefit of U.S. provisional patent applications "Semiconductor Based Mental State Analysis" Ser. No. 62/082,579, filed Nov. 20, 2014, "Viewership Analysis Based on Facial Evaluation" Ser. No. 62/128,974, filed Mar. 5, 2015, "Mental State Event Signature Usage" Ser. No. 62/217,872, filed Sep. 12, 2015, and "Image Analysis In Support of Robotic Manipulation" Ser. No. 62/222,518, filed Sep. 23, 2015.

The U.S. patent application "Image Analysis Using a Semiconductor Processor for Facial Evaluation" Ser. No. 14/947,789, filed Nov. 20, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Image Analysis Using a Semiconductor Processor for Facial Evaluation" Ser. No. 14/947,789, filed Nov. 20, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447, 464, filed Feb. 28, 2011, and "Baseline Face Analysis" Ser. No. 61/467,209, filed Mar. 24, 2011.

The U.S. patent application "Image Analysis Using a Semiconductor Processor for Facial Evaluation" Ser. No. 14/947,789, filed Nov. 20, 2015 is also a continuation-in-part of U.S. patent application "Mental State Evaluation Learning for Advertising" Ser. No. 13/708,027, Dec. 7, 2012, which claims the benefit of U.S. provisional patent applications "Mental State Evaluation Learning for Advertising" Ser. No. 61/568,130, filed Dec. 7, 2011 and "Affect Based Evaluation of Advertisement Effectiveness" Ser. No. 61/581,913, filed Dec. 30, 2011.

The U.S. patent application "Mental State Evaluation Learning for Advertising" Ser. No. 13/708,027, Dec. 7, 2012 is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Vehicle Manipulation Using Cognitive State Engineering" Ser. No. 16/429,022, filed Jun. 2, 2019, which claims the benefit of U.S. provisional patent applications "Vehicle Manipulation Using Cognitive State Engineering" Ser. No. 62/679,825, filed Jun. 3, 2018, and "Image Analysis for Human Perception Artificial Intelligence" Ser. No. 62/827,088, filed Mar. 31, 2019.

The U.S. patent application "Vehicle Manipulation Using Cognitive State Engineering" Ser. No. 16/429,022, filed Jun. 2, 2019 is also a continuation-in-part of U.S. patent application "Vehicle Manipulation using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No.

62/593,440, filed Dec. 1, 2017, and "Directed Control Transfer for Autonomous Vehicles" Ser. No. 62/611,780, filed Dec. 29, 2017.

The U.S. patent application "Vehicle Manipulation using Occupant Image Analysis" Ser. No. 15/875,644, filed Jan. 19, 2018, is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The U.S. patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The U.S. patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The U.S. patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF ART

This application relates generally to analysis of images and more particularly to image analysis using a semiconductor processor for facial evaluation in vehicles.

BACKGROUND

On any given day, an individual experiences various external stimuli, which can provoke a wide range of responses. The responses of the individual can manifest in cognitive states, mental or emotional states, facial expressions, body language, and so on. The stimuli are perceived through one or more senses and can be visual, aural, olfactory, tactile, and so on. The stimuli, whether alone or in combination, can evoke strong cognitive states or emotions in the individual who experiences those stimuli. Not all individuals in the presence of the various stimuli will react in a similar manner. That is, when a group of individuals experiences the stimuli, the reactions of the individuals can be at times substantially similar, at other times widely dissimilar, and so on. How an individual reacts to experienced stimuli can be important to defining the essence of that individual. Furthermore, the responses of the individual to the stimuli can have a profound impact on the cognitive states experienced by that individual.

The cognitive states that an individual can experience in response to external stimuli can vary depending on time frames. The time frames could be one time of day versus another, one day of the week or month versus another, and so on. An individual's cognitive state contributes to general well-being. Cognitive state further impacts her or his perception of the surrounding environment, decision-making processes, and so on. The cognitive states of multiple individuals that result from a common event can carry a collective importance. At times the collective importance of the event can be more impactful than the importance of each individual's cognitive state. The cognitive states of an individual or a group of individuals can vary widely, ranging from happiness to sadness, from contentedness to worry, and from calm to excitement, to name only a few possible states. Despite how critical and influential one's cognitive states are to daily life, the cognitive state of a single individual, let alone those of a group, might not always be apparent, even to that individual. The ability and means by which one person perceives her or his cognitive state can be quite difficult to express or summarize. Though an individual can often perceive her or his own emotional state quickly, instinctively, and with little or no conscious effort, the individual might encounter difficulty when attempting to summarize or communicate her or his cognitive state to others. This difficulty of understanding and communicating cognitive states becomes far more complex when the cognitive states of multiple individuals are considered.

Gaining an insight into the cognitive states of one or more individuals is an important technique for understanding how people react to various external stimuli. Those external stimuli can include views of the natural landscape, political and sports events, educational programs, natural disasters, etc. However, proper interpretation of cognitive states is very difficult when the individuals being considered are themselves unable to accurately identify and communicate their cognitive states. The identification and communication of cognitive states can be further complicated by the fact that multiple individuals can have similar or very different cognitive states when taking part in a communal activity. The cognitive states of two friends viewing an important political debate can be disparate. If one friend is a supporter of the winning candidate, while the other friend is a supporter of the losing candidate, it is reasonable to expect widely varying cognitive states between the two friends. The problem of defining the resulting cognitive states from multiple people experiencing complex stimuli can be a considerably complicated exercise.

SUMMARY

Modern electronic devices are constructed with a variety of special-purpose hardware that is integral to the operation of the devices. This special-purpose hardware enables the devices to support a variety of additional functions. A device such as a typical smart phone includes not only the battery, radios, and keyboard required to support telephony, SMS (text), and other common features, but also cameras, displays, haptic input devices, accelerometers, global positioning systems (GPS), audio codecs, microphones, and so on. The inclusion of this special-purpose hardware into the device vastly expands the capabilities and usefulness of the electronic devices by enabling the devices to support mapping, positioning, video communications, social networking, etc. As additional hardware is added to the electronic devices, new and emerging capabilities further expand the usefulness of the devices. Traveling in vehicles, using social media, and so on, are areas that can take advantage of many of the features and capabilities afforded by the special-purpose hardware. The GPS can be used for planning routes or locating traffic problems, or for finding friends or a favorite eatery. The display is useful for showing driving directions or for sharing pictures and videos, and so on. The cameras are used for observing operators or passengers within vehicles or making video calls and chats. Analyzing images of a person in a vehicle can also give a sense of a person's disposition to the transportation experience within a vehicle, reaction to travel conditions such as traffic or weather, mental or cognitive state such as alert or distracted, and so on. Logic devices can be used to analyze data including video data and physiological data. The data can be collected using cameras, sensors, accelerometers, and so on. When the collected data includes videos, video segments, still images, etc., then the video data in turn can be analyzed for a facial portion of one or more persons. Classifiers can be applied to facial expressions identified in the images for cognitive response content. The cognitive response content is scored to produce cognitive state information for a person in the image. The cognitive state information is communicated to a component of the vehicle in order to manipulate the vehicle.

Computational processing enables image analysis for facial evaluation in vehicles. An apparatus for analysis is described comprising: a device containing convolutional processing logic encoded in a semiconductor chip comprising: evaluation logic trained to analyze pixels within an image of a person in a vehicle, wherein the analysis identifies a facial portion of the person; identification logic trained to identify one or more facial expressions based on the facial portion; classifying logic trained to classify the one or more facial expressions for cognitive response content; scoring logic trained to evaluate the cognitive response content to produce cognitive state information for the person; and interface logic that enables manipulation of the vehicle based on communication of the cognitive state information to a component of the vehicle. Further, an additional facial portion from an image of an additional person within the vehicle is evaluated, identified, classified, and scored to produce additional cognitive state information for the additional person. The cognitive state information is augmented based on audio data or physiological data collected from within the vehicle, wherein the audio data or the physiological data is collected contemporaneously with the image.

Embodiments include a computer program product embodied in a non-transitory computer readable medium for image analysis, the computer program product comprising: code for executing on a device containing a convolutional processing logic encoded in a semiconductor chip comprising: evaluation logic trained to analyze pixels within an image of a person in a vehicle, wherein the analysis identifies a facial portion of the person; identification logic trained to identify one or more facial expressions based on the facial portion; classifying logic trained to classify the one or more facial expressions for cognitive response content; scoring logic trained to evaluate the cognitive response content to produce cognitive state information for the person; and interface logic that enables manipulation of the vehicle based on communication of the cognitive state information to a component of the vehicle.

Some embodiments include a processor-implemented method for analysis comprising: using a device containing convolutional processing logic encoded in a semiconductor chip to perform: analyzing pixels within an image of a person in a vehicle, wherein the analysis identifies a facial portion of the person; identifying one or more facial expressions based on the facial portion; classifying the one or more facial expressions for cognitive response content; evaluating the cognitive response content to produce cognitive state information for the person; and manipulating the vehicle based on communication of the cognitive state information to a component of the vehicle.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
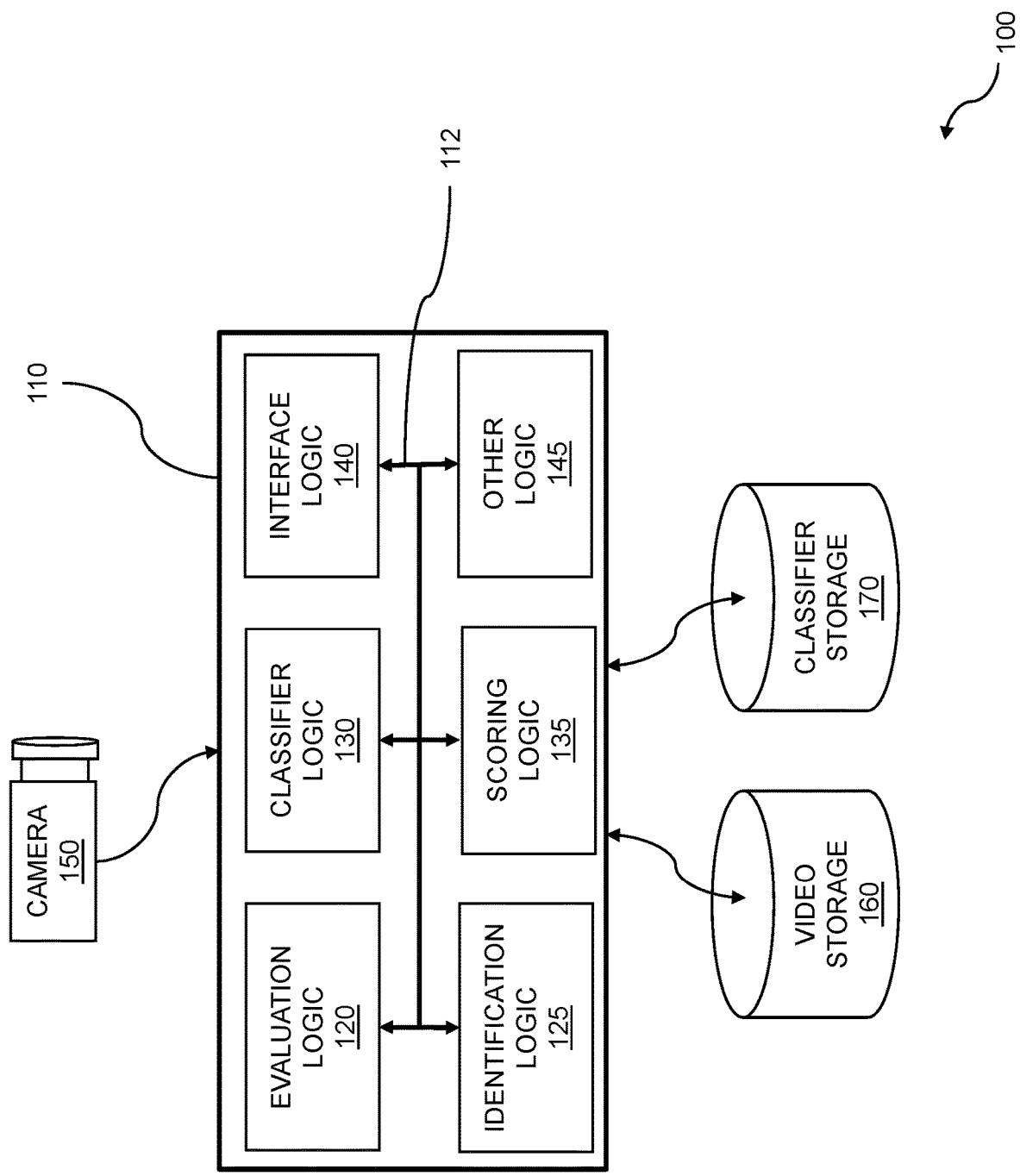
FIG. 1 is a system diagram for cognitive state analysis using facial evaluation in vehicles.

The proliferation of electronic devices, and handheld electronic devices in particular, has changed the ways in which people communicate. While smartphones still retain the functionality to communicate verbally, users of these and other electronic devices often choose to communicate via other modes. Popular communication modes that device users frequently choose include sending SMS (text) messages, using chat (voice and text) applications, posting on social media (e.g. Twitter™, Facebook™, Instagram™, etc.), and other "nontraditional" modes. According to some reports, electronic verbal communication has become non-traditional in comparison to the other modes. As a result of these user-driven changes in device usage, a wide variety of apps has been written. Further, special-purpose or custom hardware has been designed and added to the electronic devices, which greatly enhances their functionality and usefulness. This special-purpose hardware supports the popular and preferred apps and usage schemes and enables new and creative interaction modalities. A typical smartphone today includes the battery, radios, and keyboards required to support telephony, SMS (text), and other common features, plus cameras, displays, haptic input devices (3-D touch), accelerometers, global positioning systems (GPS), audio codecs, microphones, and so on. This special-purpose hardware enables the devices to perform mapping, positioning, video communications, social networking, gaming, and many other functions.

The people who use the electronic devices live and work in various regions, locations, and environments. The residences in which these people live are situated in areas as diverse as densely populated cities, sparsely populated rolling hills, open plains, woodlands, or even aboard a boat. Irrespective of whether dwellings are located in urban, suburban, or rural areas, people spend hundreds or more hours per year traveling. The traveling typically involves some sort of vehicle, where vehicles include public vehicles, private vehicles, and "alternative" vehicles. The most frequently used vehicles include public buses, trains, or airplanes; private vehicles such as automobiles or motorcycles; commercial vehicles such as taxis or ride share vehicles; and so on. Whichever vehicle is used, traveling takes time. The hours spent by individuals in vehicles are expended while commuting to and from work or school, running errands or shopping, keeping meetings and appointments, traveling, etc. The travel time erodes the opportunity for more productive pursuits such as time with friends and family, creating, or exercising.

As an individual travels, consumes media, or interacts with an electronic or computing device, that person can experience a wide range of cognitive states. The cognitive states can include drowsiness, sadness, engagement, boredom, and so on. The types and ranges of cognitive states can be determined by analyzing data, including images which include facial portion data, obtained from the person while in a vehicle. The obtained data that is analyzed can include data from multiple images, angles, or light wavelengths; facial data or torso data; audio data, voice data, speech data, or non-speech vocalizations; physiological data; and the like. The analysis can be performed using convolutional processing logic encoded in a semiconductor chip. The convolutional processing can be based on a neural network, where the neural network can be configured for deep learning. The neural network can be trained to analyze the obtained data and to identify one or more cognitive states. The neural network can be adapted or "retrained", as more data is analyzed by the network, to speed operation, to improve convergence, and so on. The convolutional processing logic can be used for image analysis for facial evaluation in vehicles.

In the disclosed materials, convolutional processing logic enables image analysis for facial evaluation in vehicles. The convolutional processing logic can be based on a neural network such as a convolutional neural network or recurrent neural network. The facial evaluation can be used to determine cognitive state information associated with a person in a vehicle. The cognitive state information associated with the person can be communicated to a component of the vehicle. The communicating to the component of the vehicle can enable manipulation of the vehicle. An individual can be observed as she or he is in the vehicle. The individual can be a vehicle passenger, an operator or driver, and so on. The individual can be interacting with the vehicle, with an electronic device or a computing device, and so on. The individual can be consuming media while traveling or on a vehicle. The cognitive state analysis is based on obtaining images that include a facial portion of the individual. The images can include video images, still images, intermittently obtained images, and so on. The images can include visible light images, near-infrared light images, etc. Facial expressions can be identified from the facial portions in the images, and the facial expressions can be classified. The classifying the facial expressions can produce content such as cognitive response content. The cognitive response content can be scored, where the scoring can produce cognitive state information. The cognitive state information can include one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state information can be used to manipulate the vehicle.

Having obtained one or more images of a person in a vehicle, an evaluation of the images is performed. Similarly, one or more images can be obtained from one or more other people within the vehicle using one or more imaging devices. The image evaluations, which can be based on analyzing pixels within an image of a person in a vehicle, can identify facial portions of the person. The facial portions can include facial landmarks; regions, or regions of interest; facial characteristics; and so on. The image evaluations can provide insight into the cognitive states of the one or more persons. All or part of the image evaluation can take place on a portable device. Through evaluation, many different cognitive states can be determined, including frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. Other cognitive states can be determined through similar evaluations. Facial expressions can be identified based on the facial portions, and classifiers can be used to produce cognitive response content. The cognitive response content is scored to produce cognitive state information. The cognitive state information can be used to manipulate the vehicle by communicating the cognitive state information to the vehicle. The cognitive state information is used to adjust or manipulate a component of the vehicle.

FIG. 1 is a system diagram for cognitive state analysis using facial evaluation in vehicles. A system 100 describes an apparatus for convolutional processing. The system 100 includes evaluation logic 120 trained to analyze pixels within an image of a person in a vehicle, wherein the analysis identifies a facial portion of the person. The semiconductor chip can include a standalone chip, a subsystem of a chip, a module of a multi-chip module (MCM), and so on. The semiconductor chip can include a programmable chip such as a programmable logic array (PLA), a programmable logic device (PLD), a field programmable gate array (FPGA), a read only memory (ROM), and so on. The semiconductor chip can include a full-custom chip design. The semiconductor chip can be reprogrammed, reconfigured, etc., "on the fly", in the field, or at any time which is convenient to the user of the semiconductor chip. The semiconductor chip can be implemented in any semiconductor technology. The evaluating of facial portions can include evaluating faces in an image, where the image can be a still image, a video, a video clip, a frame from a video, and so on. The evaluating facial portions can include scaling, rotating, translating, etc., faces within an image. In embodiments, a series of images can be supplied to the device, wherein the series of images is sourced from a video stream. The video stream can be provided by a camera or other image capture device in the vehicle.

The semiconductor chip 110 includes identification logic 125 trained to identify one or more facial expressions based on the facial portion. The facial expressions can include one or more of a smile, frown, scowl, grimace, smirk, and so on. The one or more facial expressions can convey nonverbal communication from the person. The facial portion can be based on facial landmarks such as corners of eyes or mouth, nose, ears, etc.; facial regions such as eyebrows, eyes, nose, mouth, ears, and so on; facial features such as hair obscuring facial landmarks or regions, facial hair, prosthetics such as glasses; and the like. The identifying facial expressions can be based on identifying differences in facial portions, where the facial portions can include portions of interest. The identification of differences in facial portions can be based on a histogram of gradient (HoG) evaluation. Any data representation technique can be used. The identification of differences can include evaluation of facial portion locations such as eyebrow locations. The evaluated eyebrow locations can be used to determine eyebrow raises, eyebrow furls, and so on. The identification of differences can include evaluation of eye locations. The evaluated eye locations can be used to set landmarks for eyes within the previously located face. The eye locations can be used to track eye movements, eye direction, gaze direction, head turns, head tilts, etc. The identification of differences can include evaluation of mouth locations. The evaluated mouth locations can be used to determine expressions including smiles, frowns, neutral expressions, and so on. The identification of differences can include landmark detection within the face. The detected facial landmarks can include an outer edge of a nostril, the border of the lips, the corners of the mouth, a midpoint between the eyes, etc. A Gabor filter can be utilized in the identification of differences. The Gabor filter can be used to detect edges, where the edges can include edges of regions of interest within the face, for example.

The semiconductor chip 110 includes classifier logic 130 trained to classify the one or more facial expressions for cognitive response content. The classifying can be based on using one or more classifiers, where the classifiers can be encoded in the semiconductor chip, loaded by a user of the chip, downloaded from a library or repository, and so on. The classifiers can be used to classify facial expressions into cognitive states, mental states, emotional states, moods, and so on. The classifiers can be based on statistical classifiers that include Bayesian classifiers. In embodiments, the classifiers can be light classifiers. Light classifiers can perform some classification on the semiconductor chip and work in coordination with off-chip hardware, off-chip software, and so on. In a usage example, classifiers used by the classifier logic can be used to perform all, little, or no classification on-chip, and the semiconductor chip can work in coordination with a further processor. The further processor can include a server, a cloud-based service, a distributed or mesh service, and the like. A server, for example, can be used to perform some or all of the image analysis including image analysis using classifiers. Any analysis by the server can be performed in real-time, at a later time, and so on. The cognitive states can include one or more of stress, sadness, anger, happiness, frustration, confusion, disappointment, hesitation, cognitive overload, focusing, engagement, attention, boredom, exploration, confidence, trust, delight, disgust, skepticism, doubt, satisfaction, excitement, laughter, calmness, and curiosity. The classifier logic can identify deviations from a baseline facial expression. The deviations from a baseline facial expression can indicate an individual's emotions and cognitive states. For example, suppose that several faces are located within a video. In this case, a deviation can include a difference in the facial expression of one face in comparison to the expressions of the other faces. However, note that a deviation can also include differences in the same facial expression. For example, the deviation can include an intensity of a smile or frown that differs by a set magnitude from a predetermined baseline.

The semiconductor chip 110 includes scoring logic 135 trained to evaluate the cognitive response content to produce cognitive state information for the person. The cognitive state information can include a cognitive state score based on the facial portion. The cognitive state score can be based on reactions of the person to a series of media presentations rendered with the vehicle. The cognitive state score can be based on events that occur within the vehicle or beyond the vehicle. In-vehicle events can include the media presentations, communication between or among people in the vehicle, and the like. Beyond-vehicle events can include traffic or construction delays, weather events, etc. The cognitive state score can be based on the alignment of responses to a baseline, including attunement to social norms. The cognitive state score can be based on various parameters including self-awareness, social skill, empathy, and so on. The cognitive state score can include a cognitive state, an intensity and duration of the cognitive state, and so on. The cognitive state score can provide information on happiness or another cognitive state based on the regions of the face, including a mouth, such as where the mouth is smiling. Similarly, the cognitive state score can provide information on other cognitive states including sadness, agitation, irritation, confusion, distraction, impairment, and so on. The cognitive state score can provide information on concentration based on the regions of the face, including eyebrows, such as where the eyebrows are furrowed. The cognitive state score can provide information on further cognitive states, including surprise, based on the eyebrows being raised. The device can further perform smoothing of the cognitive state score or information.

Scoring the cognitive response content can include capturing important patterns in the cognitive state information. The device can further perform image correction for the videos including one or more of lighting correction, contrast correction, or noise filtering. The image correction can be based on a variety of signal and image processing techniques including high-pass filtering, low-pass filtering, cross-correlation, etc. The cognitive state information can be augmented by audio data or physiological data. The audio data can include voice data, non-verbal vocalization data, ambient sounds within or outside of the vehicle, etc. The physiological data can include heart rate, heart rate variability, and so on. The physiological data can be gleaned from the videos of the one or more persons. The physiological data can be extracted, inferred, etc. The physiological data can also be gleaned from one or more biosensors. The biosensors can be attached to the one or more individuals and can detect physiological parameters of the individuals including heart rate, heart rate variability, respiration rate, skin temperature, skin conductivity, and so on. The cognitive state information can be used to track one or more cognitive states. The cognitive states can include one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. In some embodiments, the scoring logic further extracts one or more histogram-of-gradient (HoG) features from the regions of interest (RoI). In embodiments, the scoring logic produces the cognitive state information based on the histogram-of-gradient features.

The semiconductor chip includes interface logic 140 that enables manipulation of the vehicle based on communication of the cognitive state information to a component of the vehicle. The interface logic can comprise a register to be read directly or indirectly. The interface logic can comprise an output driver or bank of output drivers. The interface logic can comprise a more sophisticated communication interface. The communicating can be accomplished using wired or wireless techniques. In embodiments, the wireless techniques that can be used include Wi-Fi, Bluetooth®, ZigBee™, etc., and the wired techniques that can be used include Ethernet, RS-242, IEEE488™, etc. In embodiments, fiber optic transmission is used. The manipulating the vehicle can include enabling manual control, autonomous control, or semiautonomous control of the vehicle. The manipulating can include controlling devices or systems within or associated with the vehicle. In embodiments, the manipulation of the vehicle includes a locking out operation; recommending a break for an occupant; recommending a different route for the vehicle; recommending how far to drive; responding to traffic; adjusting seats, mirrors, climate control, lighting, music, audio stimuli, or interior temperature; brake activation; or steering control.

The semiconductor chip 110 includes other logic 145 that supports the semiconductor chip. In embodiments, the other logic can provide interface support for a variety of peripherals including one or more cameras, sensors including biosensors, storage devices such as disk drives (hard drives, solid state drives, optical drives, etc.), memory, (RAM, ROM, CAM, etc.), displays (video, LCD, LED, OLED, etc.), input/output devices (keyboards, trackpads, mice, touch screens, audio, etc.), and so on. The other logic can include special purpose hardware, where the special purpose hardware can be configured to execute algorithms, for example. The other logic can be reconfigurable, where the reconfiguration can be realized by programming or reencoding. The reconfiguration of the other logic can depend on algorithms, heuristics, control schemes, etc. that are stored in a storage device, entered by the user, downloaded from the Internet, and so on. The other logic supports the semiconductor chip by providing functions not supported by the other logic blocks described above. In embodiments, the other logic comprises categorization logic that updates a cognitive state profile of an individual associated with the facial portion.

The semiconductor chip 110 obtains videos, video clips, images, and so on, that are streamed from a camera 150. The camera can be any type of image capture device and can include a webcam, a video camera, a still camera, a thermal imager, a CCD device, a phone camera, a three-dimensional camera, a light field camera, multiple cameras used to obtain different aspects or views of a person or multiple persons, or any other type of image capture technique that allows captured data to be used in an electronic system. The videos and/or images can be obtained on an intermittent basis. The videos can include video frames that can be obtained by a camera coupled to the device. The camera can be built into the device. The camera can be coupled to the device using wireless techniques including Wi-Fi, Bluetooth®, ZigBee™, etc., or using wired techniques including Ethernet, RS-242, IEEE488™, etc.

The semiconductor chip 110 further includes video storage memory 160 coupled to the device. The storage memory can include read-write (RW) memory, a hard disk drive (HDD), an optical drive (OD), a solid-state disk drive (SDD), etc. The video storage memory 160 can store videos for analysis by the device, and the analysis can be used to evaluate moods, cognitive states, facial expressions, etc., for people in the videos. The videos can be obtained from the camera 150, downloaded from a network, uploaded by a user, and so on. The videos can be retrieved from the video storage memory 160 for evaluation by the convolutional logic. The videos can be retrieved using wired and wireless means. The video storage memory 160 can be coupled to a bus 112 of the chip, to a USB port, to a serial port, to a parallel port, or to another communications gateway. The video storage memory 160 can be coupled to the chip using wireless techniques as described above.

The semiconductor chip 110 further includes classifier storage memory 170 coupled to the device. As before, the classifier storage memory can include read-write (RW) memory, a hard disk drive (HDD), an optical drive (OD), a solid-state disk drive (SDD), etc. The classifier storage memory 170 can store classifiers that can be used for various processing and analysis techniques by the semiconductor device. The use of the classifiers can help evaluate cognitive states, facial expressions, mood, emotional state, and so on, of the one or more people who can be identified in the videos. The obtaining of the classifiers can take place by the classifiers being encoded in or loaded into the semiconductor chip, entered by a user, downloaded from the Internet, and so on. The classifiers can be changed at any time by recoding, reloading, reentering, re-downloading, and so on. The classifiers can be used to reprogram, reconfigure, or otherwise change or modify the chip. For example, one or more classifiers can be used to configure the other logic 145, to modify the classifier logic 130, and so on. In embodiments, the classifier storage memory stores classifier information used by the classifier logic.

Figure 2:
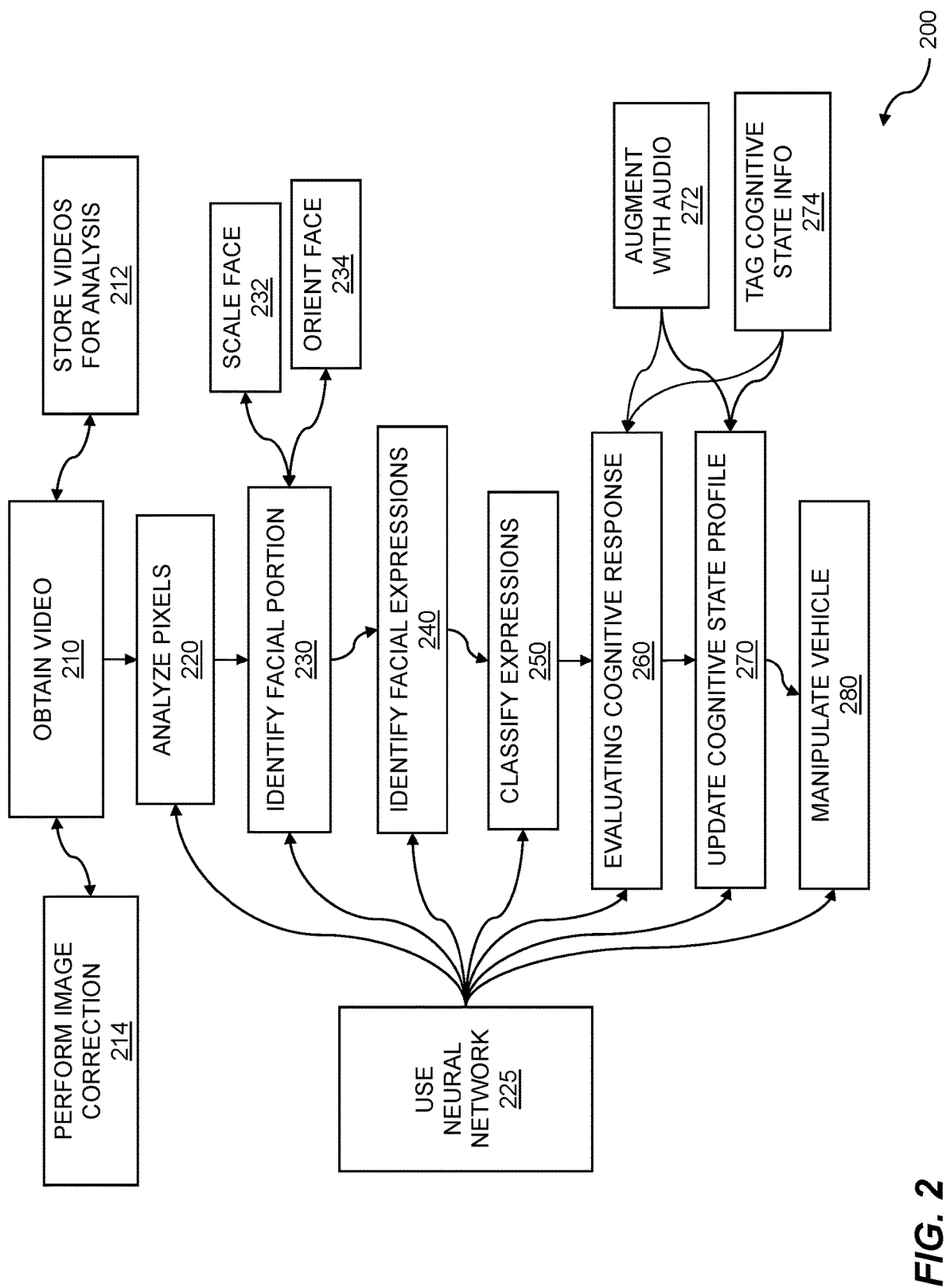
FIG. 2 is a flow diagram for cognitive state analysis.

FIG. 2 is a flow diagram for cognitive state analysis. The flow 200, or portions thereof, can be implemented using convolutional processing logic encoded in semiconductor logic. The flow 200 describes cognitive state analysis based on analysis of captured videos of one or more people in a vehicle or a plurality of vehicles. The cognitive state analysis uses the semiconductor chip for facial evaluation in vehicles. The flow 200 includes obtaining video frames 210 that are streamed from a camera. The video frames can be obtained from a video and can include one or more people. The camera can be any type of image capture device capable of capturing data to be used in an electronic system, such as a webcam, a video camera, a still camera, a thermal imager, a CCD device, a phone camera, a three-dimensional camera, a light field camera, multiple cameras to obtain different aspects or views of a person, or any other type of image capture technique. The flow 200 includes storing videos for analysis 212 to evaluate the moods of people in the videos. The videos can be stored in any appropriate storage medium including a hard disk drive, an optical drive, a solid-state drive, and so on. The videos can be stored in cloud-based storage. In embodiments, the storage medium can further include storage memory coupled to the device. The memory coupled to the device can include memory within the semiconductor chip, removable memory such as secure digital (SD) memory, flash memory, etc. As discussed below, the storage memory can store videos for analysis by the device to evaluate cognitive state information for people in the videos. The videos can be stored for later retrieval and analysis. In some embodiments, analysis of the videos is performed prior to storage. The flow 200 includes performing image correction 214 for the videos, including one or more of exposure or lighting correction, contrast correction, or noise filter smoothing. Other image corrections can be performed, including highlight correction, shadow correction, saturation correction, temperature, tint, sharpness, and so on.

The flow 200 includes analyzing pixels 220 within an image of a person in a vehicle. The videos obtained of the person in the vehicle can be partitioned into video frames, and the video frames can be analyzed. In embodiments, a series of images can be supplied to the device, wherein the series of images is sourced from a video stream. The analyzing pixels can further include analyzing pixels within still images, where the still images can include visible light images, near-infrared images, and so on. The images can include video and/or still images that are collected while the person is within the vehicle, stored images, and the like. The flow 200 includes identifying a facial portion 230 of the person. The identifying the facial portion can be based on the evaluation of pixels within the images for the presence of a facial portion within the video frames, still images, etc. When one or more persons are found to be in a frame, then further analysis of the pixels of the frame can be performed. If a person is not found in the frame, then a second video frame can be obtained and evaluated. A facial portion can include facial landmarks, facial regions, facial characteristics, and so on. The facial portion can include a full view of a facial region or a partial view of a facial region. The identifying the facial portion within an image or frame can include scaling a face 232 within the image. The scaling of the face can include magnification or zooming in, reduction or zooming out, and so on. The identifying the facial portion within the image or frame can further include orienting the face 234. The orienting of the face can include rotation of the face about any axis (e.g. x, y, or z) or any combination of axes. The scaling and the orienting of the face can be performed to improve and enhance analysis of the face.

The flow 200 includes identifying one or more facial expressions 240 based on the facial portion. The identifying one or more facial expressions can be performed for more than one facial portion. An additional facial portion can include an additional facial portion analyzed within an image resulting from a camera with a different view of the person in the vehicle. The one or more facial expressions can include a smile, a frown, a smirk, a grimace, a yawn, and so on. A facial expression can be based on one or both eyebrows raised. The flow 200 includes classifying the one or more facial expressions 250 for cognitive response content. The classifying can be accomplished using one or more classifiers, where the classifiers can be encoded in the semiconductor chip, uploaded by a user, downloaded over a network, and so on. The classifying can be based on using classifier logic. In embodiments, the classifier logic can be further trained to identify gender, age, ethnicity, or other demographic data for a face associated with the facial portion. The demographic data can be based on a yes or no determination, a range, a percentage, a threshold, etc. In embodiments, the gender, age, or ethnicity can be provided with an associated probability. The gender, age, ethnicity, and so on, can be self-provided by the person.

The flow 200 includes evaluating the cognitive response content 260 to produce cognitive state information for the person. The producing cognitive state information can be based on a score, an assigned value, a percentage, a threshold, and the like. In embodiments, the cognitive state information that was analyzed can be based on intermittent occurrences of the facial portion within a series of images. The intermittent occurrences of the facial portion can be based on techniques used to capture the video or images such as capturing video based on a time or a duration since a previous image was captured. The intermittent occurrences can be based on capturing video when line of sight is present between an imaging device and a person in the vehicle. The evaluating cognitive response content can be based on tracking logic which can identify that a face has left the images from the video stream. In further embodiments, an additional facial portion from an image of an additional person within the vehicle can be evaluated, identified, classified, and scored to produce additional cognitive state information for the additional person.

The flow 200 includes updating a cognitive state profile 270 of an individual associated with the facial portion. A cognitive state profile of an individual can include a variety of data associated with a person. In embodiments, the cognitive state profile summarizes the cognitive state information of the individual. The cognitive state profile can include one or more cognitive states such as happy, sad, distracted, impaired, etc. In embodiments, the cognitive state profile can be based on cognitive state event temporal signatures. A cognitive state event temporal signature can include an onset or intensity of the cognitive states, decay of cognitive states, duration of the cognitive states, and so on. The cognitive state profile of an individual can be compared with other cognitive state profiles of the person. In a usage example, a cognitive state profile of the person can be compared to the cognitive state profile generated for the person during previous travel within the vehicle, travel within a second vehicle, and so on. The comparison of cognitive state profiles can be used to identify changes in the cognitive states of the person such as drowsiness, impairment, distraction, and so on. The cognitive state profile for the person can be compared to cognitive state profiles of other people. The cognitive state profile can be updated based on changes in cognitive states, average cognitive states, etc. The flow 200 further includes augmenting the cognitive state information based on audio data 272 collected from within the vehicle. The audio data can be collected using a microphone, a transducer, or other audio capture device. In embodiments, the audio data can include voice data. The voice data can include speech data, non-speech vocalizations, ambient sounds within or beyond the vehicle, etc. The audio data can be collected contemporaneously with the image. In a usage example, the audio data can augment the video data to detect a yawn while the person is covering her mouth with a hand. Such augmenting can be based on coordination between the video stream and an audio stream. The cognitive state profile can further be updated based on other data collected from the person in the vehicle. The flow 200 includes tagging the cognitive state information 274 with sensor data received from the vehicle. The tagging can indicate that the person yawned while the temperature within the vehicle was too warm.

The flow 200 includes using a neural network 225 to accomplish the various elements illustrated in the flow 200, such as analyzing pixels 220, identifying facial portions 230, identifying facial expressions 240, classifying expressions 250, evaluating a cognitive response 260, and so on. Other elements within the flow 200 may be accomplished using non-neural network functionality, such as obtaining video 210, updating a cognitive state profile 270, and manipulating a vehicle 280, although neural networks may be used in these cases as well.

The flow 200 includes manipulating the vehicle 280 based on communication of the cognitive state information to a component of the vehicle. Various aspects of the vehicle can be manipulated. The manipulating the vehicle can include autonomous operation of the vehicle or semiautonomous operation of the vehicle. The manipulating the vehicle can include changing operation of the vehicle from autonomous or semiautonomous operation to manual operation of the vehicle, changing from manual operation of the vehicle to autonomous or semiautonomous operation, initiating a vehicle shutdown, and so on. In embodiments, the manipulation of the vehicle can include a locking out operation; recommending a break for an occupant; recommending a different route for the vehicle; recommending how far to drive; responding to traffic; adjusting seats, mirrors, climate control, lighting, music, audio stimuli, or interior temperature; brake activation; or steering control. The communication of the cognitive state information can include communication with the convolutional processing logic encoded within the semiconductor chip, communication with an electronic device associated with the person within the vehicle, etc. The communication can be accomplished using Wi-Fi™, LTE™, or another communication technique. In embodiments, the cognitive state information can be used to communicate one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors. Various embodiments of the flow 200 can be included on a semiconductor chip and implemented in special purpose logic, programmable logic, and so on.

Figure 3:
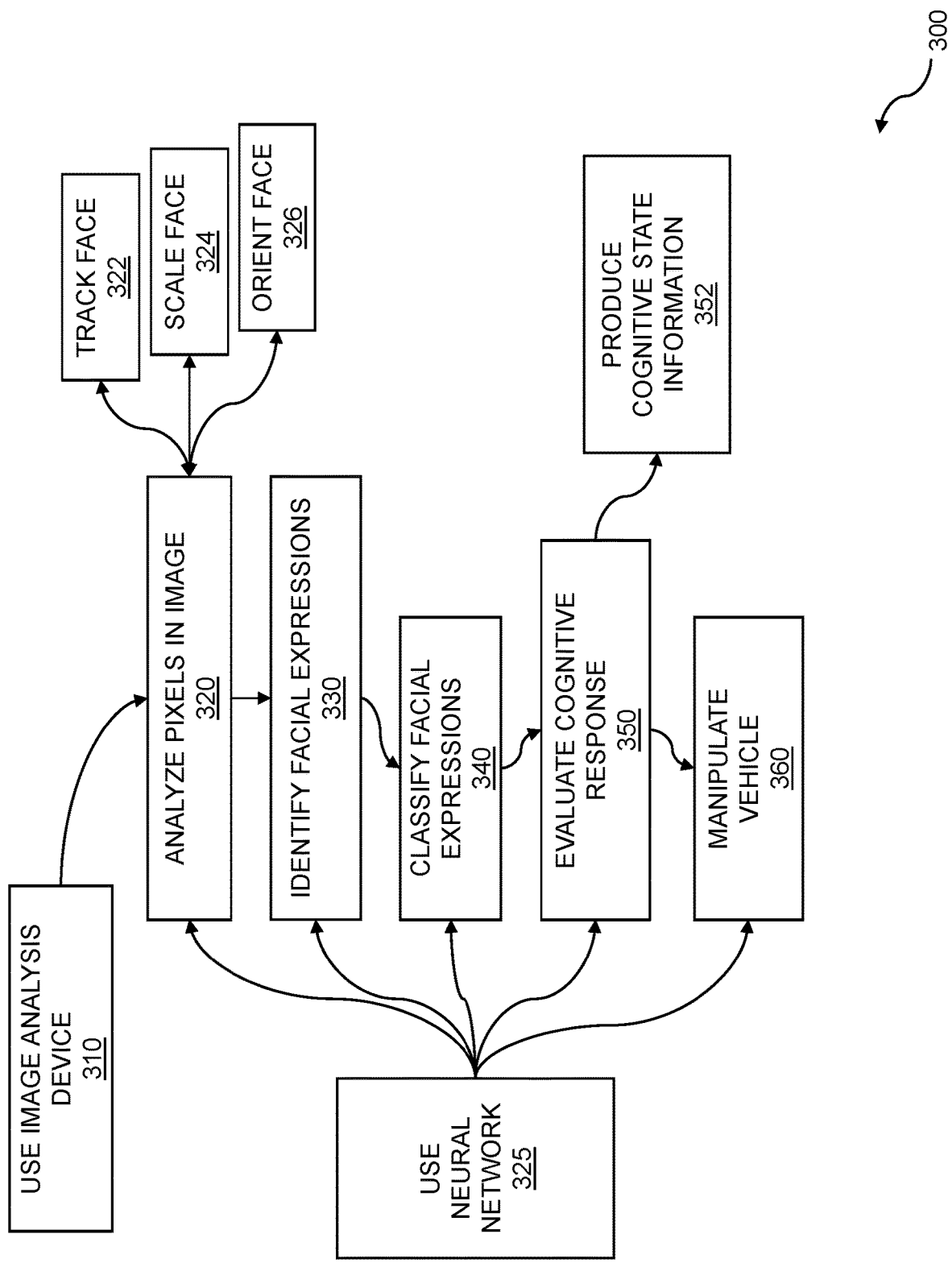
FIG. 3 is a flow diagram for convolutional processing device usage.

FIG. 3 is a flow diagram for convolutional processing device usage. Convolutional processing, which can be accomplished using logic encoded within a device such as a semiconductor chip, can accomplish image analysis. The image analysis can enable facial evaluation in vehicles. In embodiments, images of one or more persons in a vehicle can be obtained. An image can be analyzed, where the analysis identifies a facial portion of the person. One or more facial expressions can be identified based on the facial portion. The facial expressions can be classified for cognitive response content, and the cognitive response content can be scored to produce cognitive state information for the person. The vehicle can be manipulated based on communication of the cognitive state information to a component of the vehicle. In embodiments, the vehicle includes an autonomous vehicle or a semiautonomous vehicle. The component of the vehicle can include lighting, climate controls, entertainment controls, lock-out based on vehicle operator impairment, and so on.

The flow 300, or portions thereof, can be implemented by encoding logic in semiconductor chip. The logic that is encoded can include evaluation logic, identification logic, and so on, where the various encoded logics can accomplish convolutional processing for analysis such as image analysis. The flow 300 includes using an image analysis device 310 that contains image analysis logic encoded in a semiconductor chip. The semiconductor chip can be used to determine cognitive states by analyzing captured videos of one or more people, as previously described. The videos can include a video feed or another video source, where the video feed can be made up of video frames that can be streamed from a camera. The video frames can be extracted from a video, and the video frames can include one or more people. The video frames can be based on video that includes intermittent occurrences of a facial portion within a series of images. The camera can be any type of image capture device capable of capturing data to be used in an electronic system. The camera can include a webcam, a video camera, a still camera, a thermal imager, a CCD device, a phone camera, a three-dimensional camera, a light field camera, multiple cameras to obtain different aspects or views of a person, or any other type of image capture technique.

The flow 300 includes training evaluation logic to analyze pixels within an image 320 of a person in a vehicle. The analysis identifies a facial portion of the person. The evaluation logic that performs the analysis of pixels can be used to determine whether one or more facial portions are present within a given video frame. When one or more facial portions are found, then analysis can be performed on the video frame. When no facial portions are located within the given frame, the next frame can be obtained. A determination can be made as to whether analysis can be performed for this next video frame. Recall that the absence of one or more facial portions within a given frame can indicate that the one or more facial portions present in a prior frame have exited the current frame. In this case, identifiers determined for a prior frame can be retained in the event that one or more facial portions return in a future frame. Discussed throughout, convolutional processing, which can include convolutional logic, can comprise one or more techniques that can be used for image analysis. In embodiments, the convolutional processing logic comprises a deep neural network. The deep neural network can accomplish deep learning, where the deep learning can be applied to image analysis. The flow 300 includes using a neural network 325 for the analyzing pixels within the image. Discussed below, the use of a neural network such as a deep neural network, is applied to other image analysis techniques.

The identification of a facial portion within an image of a person in a vehicle can be accomplished by analyzing pixels within the image, using a sliding a window, using edge detection, or another technique. The window can include a window of any size and shape appropriate to the identifying the facial portion. The flow 300 further includes using the convolutional processing device for tracking 322 the facial portion. The tracking can be based on tracking logic. The tracking the facial portion can include tracking between images, between video frames, and so on. In embodiments, tracking logic can be trained for tracking the facial portion and identifying that the facial portion is no longer within images from the video stream. A facial portion might no longer be within an image due to a person turning away, leaning down, exiting a vehicle, changing positions within the vehicle, and so on. In embodiments, the tracking logic can identify that a face has left the images from the video stream. In a usage example, a person can stop a vehicle and can exit the vehicle for various purposes such as shopping, eating, fueling the vehicle, and so on. The person can then return to the vehicle when the task has been completed. In embodiments, the tracking logic can identify that the face has returned to the images from the video stream and can associate information previously collected about the face before the face left the video stream. As previously discussed, the convolutional processing device can be used to track one or more facial portions of one or more faces, where the portions can include identifying eyes, eyebrows, ears, a nose, a mouth, a chin, and so on. The facial portions can include identifying characteristics, distinguishing marks, etc. The flow 300 further uses the convolutional processing device to perform scaling of a facial feature 324. Scaling of the facial feature can include zooming in (magnifying), zooming out (shrinking), and other sizing and resizing techniques. The scaling can be performed on the one or more facial portions that can be identified in the one or more images. The flow 300 further uses the convolutional processing device to orient the face 326. Orienting the face can include rotation of the face about an axis (e.g. x, y, and z axes), tilting a face, and so on. In other embodiments, the device can further perform image correction for the image including one or more of lighting correction, contrast correction, near infrared lighting correction, or noise filtering. The image correction can compensate for low light conditions, changeable light conditions, partially obscured views from one or more cameras to a person, etc. The image correction can be based on a variety of signal and image processing techniques including high-pass filtering, low-pass filtering, band-pass filtering, cross-correlation, etc.

The flow 300 includes identifying one or more facial expressions 330 based on the facial portion. The device containing convolutional processing logic can be used to perform various algorithms and heuristics to identify facial expressions. The facial expressions can be based on determining facial landmarks, facial regions, facial characteristics, and so on. The determining facial expressions can be based on determining one or more action units (AUs). The determining facial expressions can be based on detecting an onset, a duration, a decay, an intensity, and so on, associated with a facial expression. The facial expressions can include a neutral expression, a smile, a frown a smirk, and so on. The flow 300 includes classifying the one or more facial expressions 340 for cognitive response content. The classifying can be based on using classifying logic that can be trained or encoded to perform one or more classifying techniques. The classifying can be accomplished using one or more classifiers that can be included in the semiconductor chip, code that can be operated on by the semiconductor chip, and the like. The classifiers can be uploaded by a user, downloaded from a networked or cloud-based repository, etc. The cognitive state content can be based on which facial expressions occurred, the intensities and/or durations of the facial expressions, and the like. The classifying can be based on demographic information. In embodiments, the classifier logic can be further trained to identify a gender, age, ethnicity, or other demographic information, for a face associated with the facial portion. The identification of demographic information can be based on value, a threshold, a range of values, etc. In embodiments, the gender, age, or ethnicity can be provided with an associated probability. In other embodiments, the device can send one or more images to a web service for external classification based on the cognitive state information. The web service can include a subscription or contract service.

The flow 300 includes evaluating the cognitive response content 350. The evaluating the cognitive response content can be accomplished using the device containing convolutional processing logic. In embodiments, the cognitive response content includes facial expressions. The cognitive response content can further include an attitude or tilt of a head, a direction of gaze, and the like. The cognitive response content can be evaluated based on a value, a percentage, a range of values, and so on. The evaluating can be based on scoring, where a score can be assigned to cognitive response content. The cognitive response score can be based on the alignment of responses to a baseline, including attunement to social norms, in some cases. Various parameters can be used as a basis for determining the cognitive response score. For example, the parameters can include self-awareness, social skill, and empathy. The cognitive response score can include an emotion, an intensity of the emotion, and so on. The cognitive response score can provide information, such as information on happiness, based on the regions of the face. The regions of the face can include a mouth where the mouth is smiling, neutral, frowning, smirking, etc. Similarly, the cognitive response score can provide information on other emotions including sadness, agitation, irritation, confusion, and so on. The cognitive response score can provide information on concentration based on the regions of the face including eyebrows, where the eyebrows are furrowed. The emotion score can provide information on other emotions including surprise, based on the eyebrows being raised.

In the flow 300, the cognitive response content is evaluated to produce cognitive state information 352 for the person. The cognitive state information can be used to relate or communicate one or more cognitive states. In embodiments, the cognitive state information can be used by a software application running on a processor coupled to the device. The application can also be running on a server; on a remote processor available to the device; through a network such as a computer network, a cloud, or mesh processor; etc. In embodiments, the cognitive state information can be used to communicate one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state information can be augmented using further data collected in a vehicle. Embodiments further include logic for augmenting the cognitive state information based on audio data collected from within the vehicle, where the audio data is collected contemporaneously with the image. The cognitive state information can also be augmented with physiological data. The physiological data can be collected using sensors, cameras, and so on. In embodiments, physiological information can be gleaned from a video containing the image. The cognitive state information can be processed, analyzed, stored, and so on. In embodiments, the device can further perform smoothing of the cognitive state information.

The flow 300 includes manipulating the vehicle 360 based on communication of the cognitive state information to a component of the vehicle. The communication of the cognitive state information can be accomplished using wireless techniques such as Wi-Fi™ Long Term Evolution (LTE™), and so on. The cognitive state information can be communicated to an electronic device such as a smartphone associated with the person in the vehicle. The component of the vehicle can include equipment position adjustments, vehicle climate control, vehicle entertainment center control, media suggestions, and so on. The component of the vehicle can be associated with other manipulation controls of the vehicle such as autonomous control, semiautonomous control, etc. In embodiments, the manipulation of the vehicle can include a locking out operation; recommending a break for an occupant; recommending a different route for the vehicle; recommending how far to drive; responding to traffic; an adjusting of seats, mirrors, climate control, lighting, music, audio stimuli, or interior temperature; brake activation, or steering control.

Figure 4:
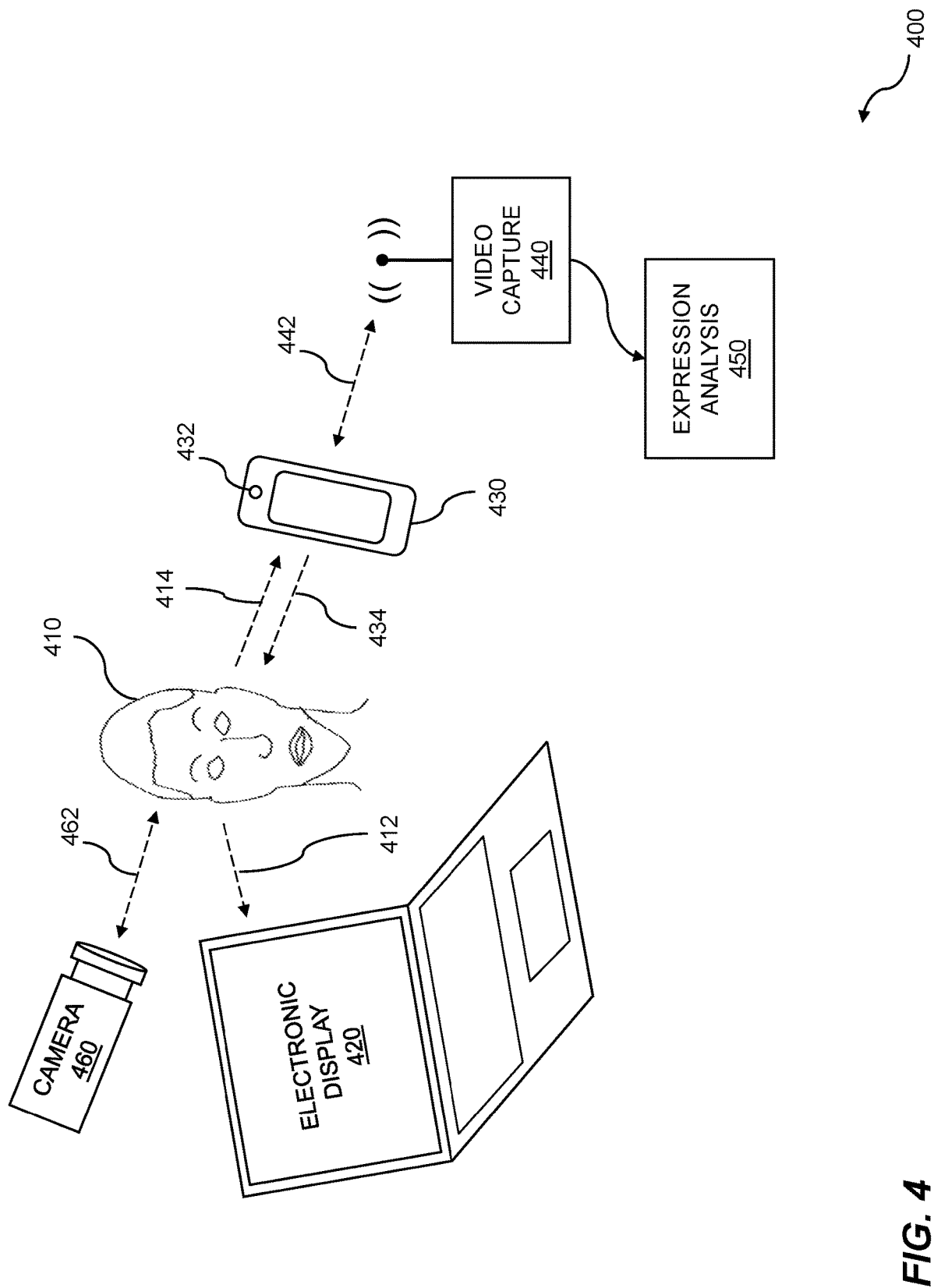
FIG. 4 illustrates image collection for cognitive state analysis.

FIG. 4 illustrates image collection for cognitive state analysis. Image collection can be accomplished using a webcam, a video camera, a still camera, or another image capture device. The captured images can be analyzed using a semiconductor processor for facial evaluation of one or more persons within a vehicle. The semiconductor processor or chip can include a semiconductor chip within a device comprising one or more semiconductor chips. The device can include a computing device such as a laptop computer, a mobile device 430 such as a smartphone, tablet, or PDA, and so on. The example 400 shows a person 410 viewing an event on one or more electronic displays such as electronic display 420. In practice, any number of displays can be shown to the person 410. An event can be a media presentation, where the media presentation can be viewed on an electronic display. The media presentation can include an advertisement, a political campaign announcement, a TV show, a movie, a video clip, a slide show, an educational program, or any other type of media presentation. In the example 400, the person 410 has a line of sight 412 to an electronic display 420. Similarly, the person 410 also has a line of sight 414 to the display of the mobile device 430. While one person has been shown, in practical use, embodiments of the present invention can analyze groups of people comprising tens, hundreds, or thousands of individuals or more. In embodiments including groups of people, each person has a line of sight 412 to the event or media presentation rendered on the digital display 420, and/or each person has a line of sight 414 to the event or media presentation rendered on a digital display of the mobile device 430. The plurality of captured videos can be of people who are viewing substantially identical media presentations or events, or conversely, the videos can capture people viewing different events or media presentations.

The display 420 can comprise a television monitor, a projector, a computer monitor (including a laptop screen, a tablet screen, a net book screen, etc.), a projection apparatus, and the like. The portable device display 430 can include a cell phone display, a smartphone display, a mobile device display, a PDA display, a tablet display, or another electronic display. A camera can be used to capture images and video of the person 410. In the example 400, a camera 432 coupled to the mobile device 430 has a line of sight 434 to the person 410. Other cameras can be used, including a webcam, a room camera, a wireless camera, etc. In embodiments, a room camera 460 or web camera has a line of sight 462 to the person 410. In a usage example, the webcam can be a networked digital camera that can take still and/or moving images of the face and possibly the body of the person 410. The device camera 432 can be used to capture one or more of the facial data and the physiological data.

The camera 432 coupled to the mobile device 430 can be used to capture data from the person 410. In embodiments, the camera 432 or multiple cameras are used to capture data from a plurality of people. The camera 432 can be built into the device or can be separate from but linked to the device. The camera 432 can refer to any camera, including a camera on a computer (such as a laptop, a netbook, a tablet, or the like), a video camera, a still camera, a 3-D camera, a thermal imager, a CCD device, a three-dimensional camera, a light field camera, multiple webcams used to show different views of the viewers, or any other type of image capture apparatus that allows captured image data to be used in an electronic system. In addition, the camera 432 can refer to a cell phone camera as shown, a mobile device camera (including, but not limited to, a front-side camera and a back-side camera), and so on. The camera 432 can capture a video or a plurality of videos of the person or persons viewing the event or situation displayed on the electronic display 420. The plurality of videos can be captured of people who are viewing substantially identical situations, such as viewing media presentations or events. The videos can be captured by a single camera, an array of cameras, randomly placed cameras, a mix of camera types, and so on. As mentioned above, media presentations can comprise an advertisement, a political campaign announcement, a TV show, a movie, a video clip, an educational program, or any other type of media presentation. The media can be oriented toward an emotion. For example, the media can include comedic material to evoke happiness, tragic material to evoke sorrow, and so on.

A video capture module 440 can receive the facial data collected by the camera 432, the camera 460, and so on. The facial data can be received using a wired network, a wireless link 442, or other communication technique. The wireless link can be based on Wi-Fi™, Bluetooth™, Zigbee™ NFC™ and so on. The video data can include streamed video data, where the videos can be streamed from the camera 432. The videos can include video frames obtained by the camera 432. The video capture module 440 can decompress the video into a raw format from a compressed format such as H.264, MPEG-2, or the like. Facial data that is received can be received in the form of a plurality of videos, with the plurality of videos coming from a plurality of devices, cameras, etc. The plurality of videos can be of one person and/or of a plurality of people who are viewing substantially identical situations or substantially different situations. The facial data can include information on action units, head gestures, eye movements, muscle movements, expressions, smiles, and the like.

The raw video data can then be processed for expression analysis 450. The processing can include analysis of expression data, action units, gestures, cognitive states, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, such as a head tilt to the side, a forward lean, a smile, a frown, as well as many other gestures. Other types of data including physiological data can be obtained, where the physiological data can be obtained through the camera 432 without contacting the person or persons. Respiration, heart rate, heart rate variability, perspiration, temperature, and other physiological indicators of cognitive state can be determined by analyzing the images and the video data. All of this analysis can be implemented and performed, or augmented by, semiconductor logic.

Figure 5:
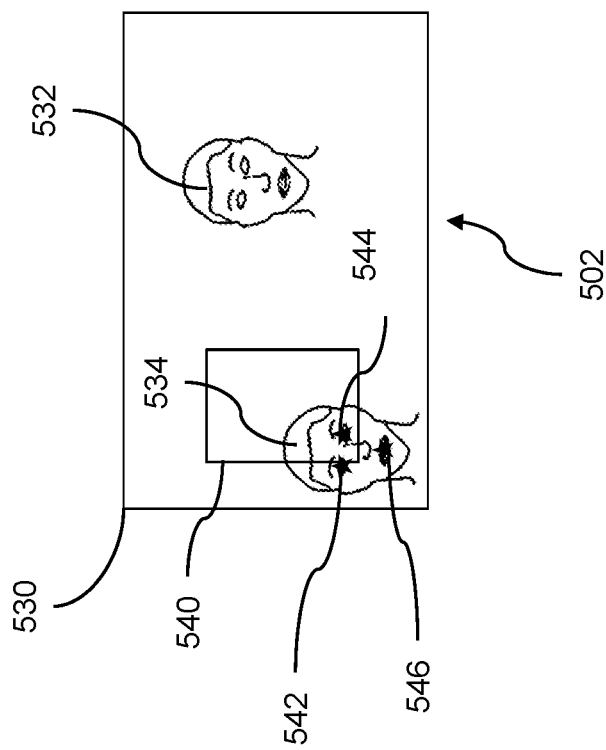
FIG. 5 is an example showing a second face.
Figure 5:
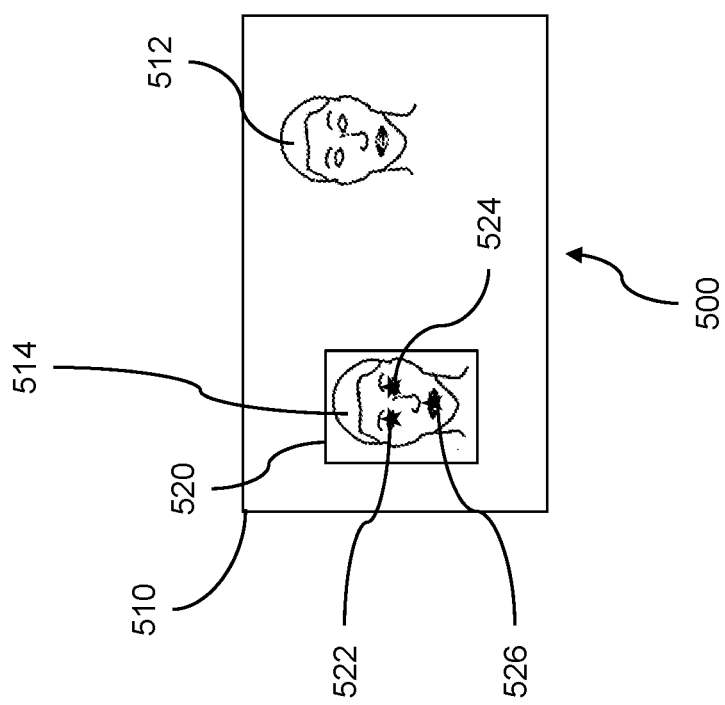

FIG. 5 is an example showing a second face and associated detection. Such detection and analysis can be performed by a device such as a device based on semiconductor logic. A device such as an analysis device can be used to perform face detection for a second face within an image, as well as facial tracking between images. Analysis and detection of a second face can enable facial evaluation in vehicles. A facial portion of a person can be identified by analyzing pixels within an image of a person in a vehicle. One or more facial expressions can be identified based on the facial portion, and the one or more facial expressions can be classified for cognitive response content. The cognitive response content can be scored to produce cognitive state information for the person, and the vehicle can be manipulated based on communication of the cognitive state information to a component of the vehicle.

One or more videos, video clips, still images based on visible or near-infrared light, and so on, can be captured using one or more imaging devices. The imaging devices can be located within a vehicle, within a second vehicle, beyond the vehicle, and so on. The one or more captured videos can contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code, for example, by analyzing a known set of data, known as a training set. The training set can include data for which category memberships of the data can be known. The training set can be used as part of a supervised training technique. If a training set is not available, then a clustering technique can be used to group observations into categories. This latter approach, or unsupervised learning, can be based on a measure (i.e. distance) of one or more inherent similarities among the data that is being categorized. When the new observation is received, then the classifier can be used to categorize the new observation. Classifiers can be used for many analysis applications including analysis of one or more faces. The use of classifiers can be the basis of analyzing the one or more faces for gender, ethnicity, and age; for detection of one or more faces in one or more videos; for detection of facial features; and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques for performing classification exist. For example, classification of one or more observations into one or more groups can be based on distributions of the data values, probabilities, and so on. Classifiers can be binary, multiclass, linear, and so on. Algorithms for classification can be implemented using a variety of techniques including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 5, the detection of the second face can include identifying facial landmarks, generating a bounding box, and predicting a bounding box and landmarks for a next frame, where the next frame can be one of a plurality of frames of a video containing faces. A first video frame 500 includes a frame boundary 510, a first face 512, and a second face 514. The frame 500 also includes a bounding box 520. Facial landmarks can be generated for the first face 512. Face detection can be performed to initialize a second set of locations for a second set of facial landmarks for a second face within the video. Facial landmarks in the video frame 500 can include the facial landmarks 522, 524, and 526. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face and can include estimating a second rough bounding box for the second face based on the facial landmark detection. For example, the estimating of a second rough bounding box can include the bounding box 520. Bounding boxes can also be estimated for one or more other faces within the frame 510. The bounding box can be refined, as can one or more facial landmarks. The refining of the second set of locations for the second set of facial landmarks can be based on localized information around the second set of facial landmarks. The bounding box 520 and the facial landmarks 522, 524, and 526 can be used to estimate future locations for the second set of locations for the second set of facial landmarks in a future video frame from the first video frame.

A second video frame 502 is also shown. The second video frame 502 includes a frame boundary 530, a first face 532, and a second face 534. The second frame 502 also includes a bounding box 540 and the facial landmarks 542, 544, and 546. In other embodiments, any number of facial landmarks are generated and used for facial tracking of the two or more faces of a video frame, such as the shown second video frame 502. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to differentiate between the first face and the second face, to track either or both of the first face and the second face, and so on. Other facial points can correspond to the second face. As mentioned above, any number of facial points can be determined within a frame. One or more of the other facial points that are determined can correspond to a third face. The location of the bounding box 540 can be estimated, where the estimating can be based on the location of the generated bounding box 520 shown in the prior frame 500. The three facial points shown, facial points 542, 544, and 546, might lie within the bounding box 540 or might not lie partially or completely within the bounding box 540. For example, the second face 534 might have moved between the first video frame 500 and the second video frame 502. Based on the accuracy of the estimating of the bounding box 540, a new estimation can be determined for a third, future frame from the video, and so on. The evaluation can be performed, all or in part, on semiconductor-based logic.

Figure 6:
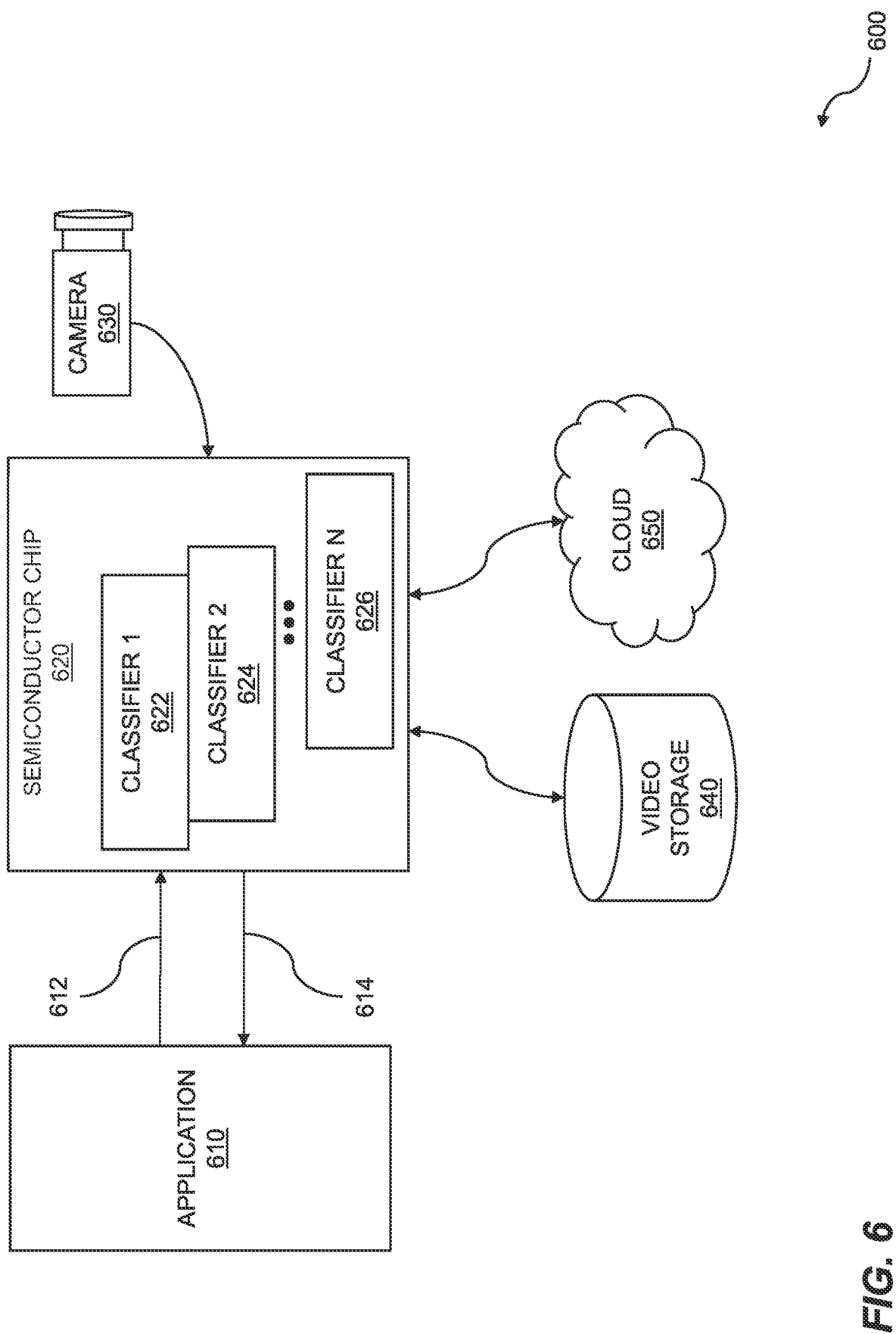
FIG. 6 illustrates a semiconductor chip with classifiers.

FIG. 6 illustrates a semiconductor chip with classifiers. One or more classifiers can be used to analyze images that include facial information. The classifiers can be used to locate a facial landmark, region, or feature; to determine facial expressions; and so on. Classifiers for image analysis can use a semiconductor processor for facial evaluation in vehicles. Pixels within an image of a person in a vehicle are analyzed, where the analysis identifies a facial portion of the person. One or more facial expressions are identified based on the facial portion. The one or more facial expressions are classified for cognitive response content. The cognitive response content is scored to produce cognitive state information for the person. The vehicle is manipulated based on communication of the cognitive state information to a component of the vehicle.

In the diagram 600, an application 610, hereafter referred to as an app, is shown loaded onto a device. The device can include any of a range of devices, such as portable devices including laptop computers and ultra-mobile PCs; mobile devices such as smartphones, PDAs, and tablets; and wearable devices such as glasses and wrist watches, etc. Any number of apps can be loaded or running on the device. The apps can include a social networking app, such as Facebook™, Digg™, Google+™ LinkedIn™, Tumblr™, Foursquare™, Yelp™, Waze™ and so on. Numerous other types of apps can likewise utilize emotional enablement. Emotional enablement of an app can allow a user to automatically express her or his emotions while using the app. In many cases, the devices contain built-in cameras, but some devices might employ external cameras that are connected to the device, accessible by the device, and so on. The semiconductor chip with classifiers can enable image analysis for facial evaluation in vehicles. The facial evaluation can include identifying a facial portion of a person in an image by analyzing pixels within the image. Facial expressions can be identified based on the facial portion, and the facial expressions can be classified for cognitive response content. The cognitive response content can be scored to produce cognitive state information, and the vehicle can be manipulated based on communication of the cognitive state information to a component of the vehicle.

In the example shown, an app 610 communicates with a semiconductor chip 620 which allows for emotionally enabling the app. In some embodiments, the semiconductor chip is a stand-alone chip, a custom chip, an FPGA, a module included in a chip, and so on. The semiconductor chip 620 shown includes multiple classifiers to process cognitive state data and infer cognitive states. The classifiers can be employed to map the regions within a face for emotional content. The cognitive states can include one or more of stress, sadness, anger, happiness, frustration, confusion, disappointment, hesitation, cognitive overload, focusing, engagement, attention, boredom, exploration, confidence, trust, delight, disgust, skepticism, doubt, satisfaction, excitement, laughter, calmness, and curiosity. One or more cognitive states can be analyzed to determine emotional states, moods, and other useful information which can prove difficult for an individual to self-identify. In embodiments, one or more classifiers are present in a semiconductor chip. In the figure shown, three example classifiers are present: classifier 1 622, classifier 2 624, and classifier N 626. While classifiers are typically code or data from a cloud or another remote source, classifiers can be stored locally on the semiconductor chip in some cases. In embodiments, any number of classifiers is possible. The classifiers can be obtained from any of a variety of sources, including by Internet download, from an application vendor site, from user-developed code, and so on. Similarly, new classifiers can be obtained from a variety of sources. The classifiers in the semiconductor chip can be updated automatically. The classifiers can be used to identify deviations from a baseline facial expression. The baseline facial expression can be a standard facial expression, a typical facial expression for a person, and so on.

Various communication channels can exist between an app and the semiconductor chip. For example, the app 610 can communicate with the semiconductor chip 620 via a channel 612 and can receive a communication back from the semiconductor chip via the same channel or another channel, such as a second channel 614. The semiconductor chip 620 can receive an initialization instruction or another communication through the channel 612 from the app 610. The semiconductor chip can perform various operations based on the initialization. The operations performed can include one of more of the classifiers 1 622 through N 626. The operations performed can include mapping the regions within the face for emotional content and evaluating the emotional content to produce an emotion score based on the face and the mapped regions. Information on the one or more emotional states, on the mapping of the regions within the face for emotional content, and on the evaluating the emotional content to produce an emotion score, etc. can be returned to the app 610 using the second channel 614.

The semiconductor chip 620 can use classifiers to process and analyze cognitive state data gathered from a user or users. In embodiments, the data is in the form of an image or video of the user or users. The image or video can be obtained from a variety of sources, including one or more cameras 630, video file storage systems 640, or cloud-based resources 650, and can be obtained using a variety of networking techniques, including wired and wireless networking techniques. In embodiments, the images are from a collection of photographs, an album, or another grouping of images or videos. The application can pass parameters or information on the source of the video or images that contain cognitive state data to the semiconductor chip. Cognitive state information, when analyzed from the cognitive state data, can aid individuals in identifying emotional states and moods. In embodiments, the app 610, semiconductor chip 620, camera 630, and video file storage systems 640 reside on the same device.

The classifiers 622, 624, and 626 can be utilized by support vector machine analysis to identify the emotional content. The support vector machine can be used for machine learning. The support vector machine can include supervised learning models and learning algorithms and can be used to analyze the emotional content for the classification. The support vector machine can use a pre-trained algorithm. The algorithm can be used to identify the emotional content. In some embodiments, the pre-trained algorithm serves as a starting point in the machine learning and can be modified to improve identification of the emotional content. The support vector machine can generate the emotion score. The emotion score can be used by a software application running on a processor coupled to the device or semiconductor chip 620. In embodiments, the emotion score can be used directly by accessing special hardware included in the semiconductor chip 620. In some embodiments, the classifiers on the semiconductor chip can be lighter or simpler versions that can assist in sifting image data. Then a fuller set of classifiers can be performed on web-based servers, if warranted.

Figure 7:
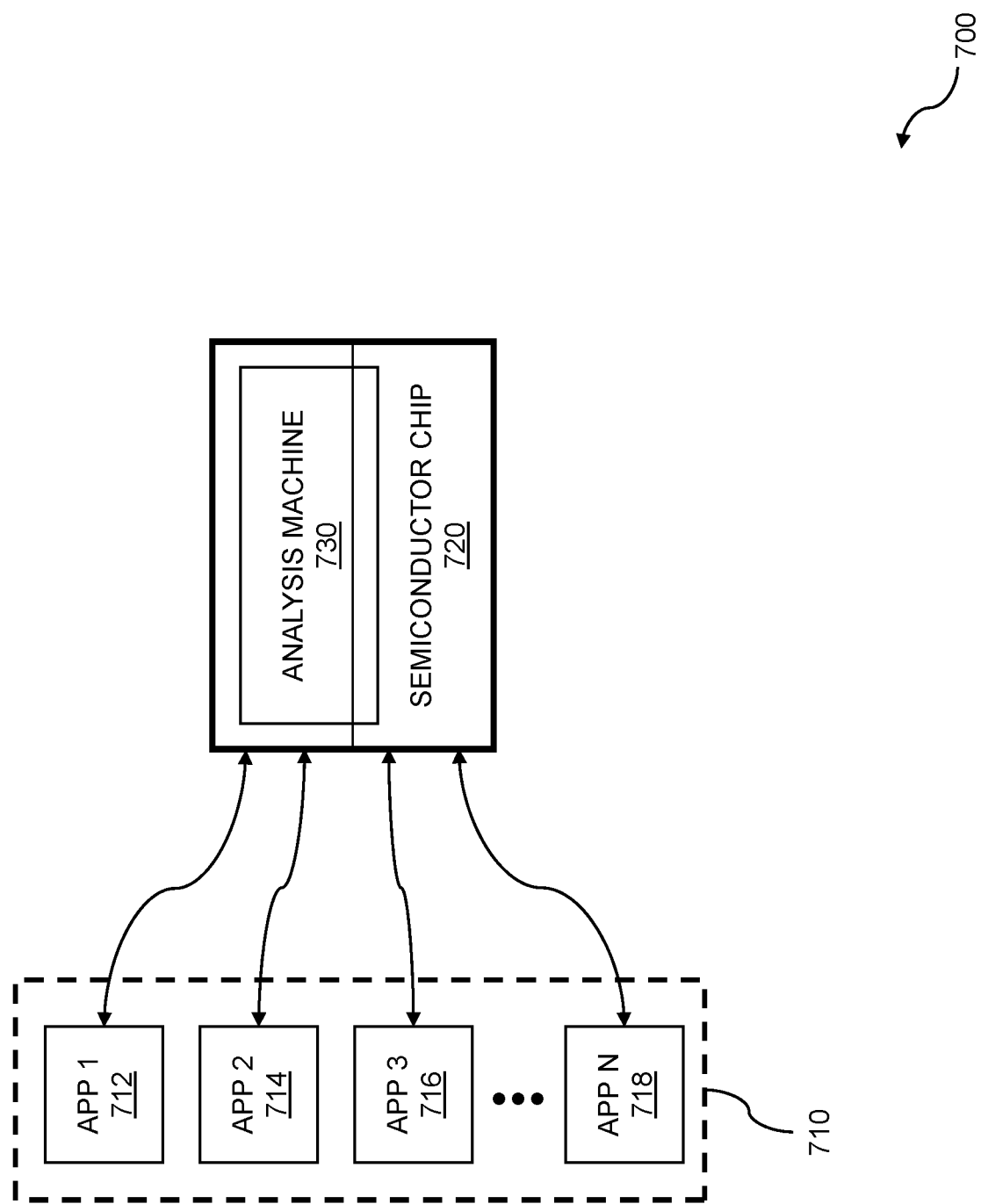
FIG. 7 shows apps calling the semiconductor chip analysis machine.

FIG. 7 shows apps calling the semiconductor chip analysis machine. Programs, processes, routines, applications, apps, and so on, can be processed on a semiconductor chip. In the example 700, one or more apps 710 call a semiconductor chip 720. The apps can include image processing apps which use the semiconductor chip for facial evaluation in vehicles. Pixels within an image of a person in a vehicle can be analyzed to identify a facial portion of the person. Facial expressions can be identified based on the facial portion, and the facial expressions can be classified for cognitive response content. The cognitive response content can be scored to produce cognitive state information, and the vehicle can be manipulated based on communication of the cognitive state information to a component of the vehicle. The apps such as the image analysis apps can reside on a device, where the device can be a portable device such as a laptop or ultra-mobile PC; a mobile device such as a smartphone, tablet, or personal digital assistant (PDA); a wearable device such as glasses or a watch; and so on. In embodiments, the apps 710 and the semiconductor chip 720 reside on the same device. The apps 710 can include a single app, such as an app 1 712. In some embodiments, the apps 710 comprise a plurality of applications, such as an app 1 712, an app 2 714, an app 3 716, an app N 718, and so on. The apps can comprise any of a variety of apps, including social media apps. The semiconductor chip 720 can provide emotional enablement to a device on which the semiconductor chip 720 resides. A user can choose to emotionally enable any number of apps loaded on her or his device. The one or more apps 710 can send video, images, raw data, or other user information to the semiconductor chip 720 for analysis. The images, video, user information, and the like can be generated by the device, obtained by the device, loaded onto the device, and so on.

The semiconductor chip 720 can include analysis capabilities in the form of an analysis machine 730. In some embodiments, the semiconductor chip 720 also communicates with other devices and services, including a web service. Analysis of raw data can be performed on the device, on the web service, or on both the device and the service. The raw data can include images, video, video clips, user information, and so on. In at least one embodiment, all of the analysis needed by the one or more apps 710 is performed on the device. The analysis machine 730 can analyze the image or video to determine one or more cognitive states, where the cognitive states can include one or more of stress, sadness, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, and curiosity. The analysis machine 730 can determine one or more emotional states based on the cognitive state information. The analysis machine 730 can employ classifiers to map the regions within a face for emotional content. The classifiers can include facial expressions such as happy, sad, angry, fearful, etc., as well as information such as race, gender, and so on. The classifiers can map facial regions including the mouth, eyes, eyebrows, etc. The analysis machine can evaluate emotional content to produce an emotion score based on the face. The emotion score can be used by a software application running on a processor coupled to the device or semiconductor chip 720. In another embodiment, a hardware module coupled to the semiconductor chip 720, or incorporated into the chip, can use the emotion score. The emotion score can be used to rank the intensity of the facial expressions, for example.

Figure 8:
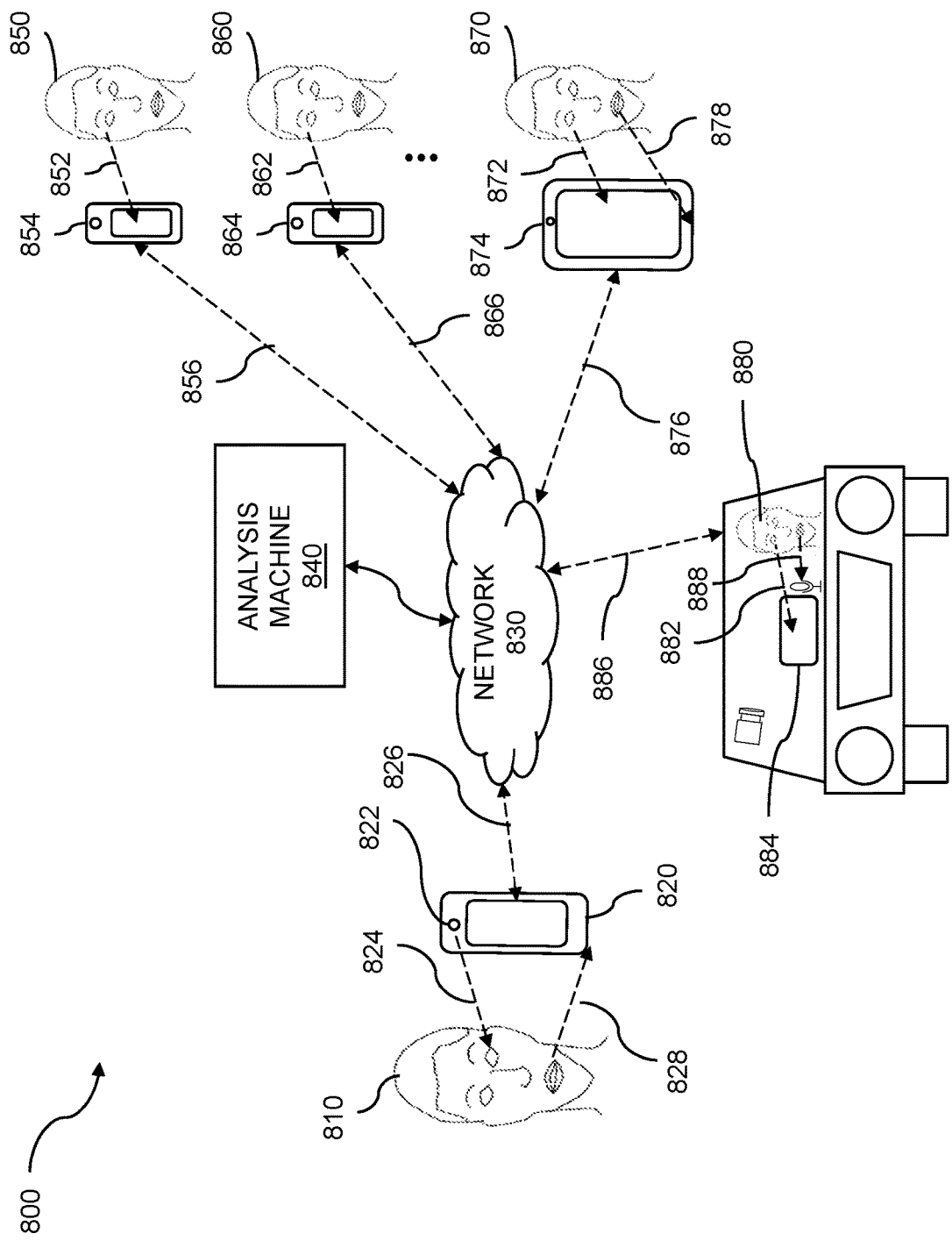
FIG. 8 illustrates an example of live streaming of social video and audio.

FIG. 8 shows an example of live streaming of social video and audio. The streaming of social video and social audio can be applied to image analysis based on convolutional processing techniques encoded in a semiconductor chip. The image analysis enables facial evaluation in vehicles. The live streaming can include cognitive state data, imaging data, facial data, upper torso data, speech data, audio data, physio data, etc. Images that include facial data for cognitive state analysis can be obtained based on a variety of image capture techniques such as in-vehicle imaging devices, cameras beyond a vehicle that have a view of the vehicle, and so on. An image of a person in a vehicle is analyzed to identify a facial portion of the person, such as facial regions, facial landmarks, and so on. One or more facial expressions are identified based on the facial portion, and the one or more facial expressions are classified for cognitive response content. The cognitive response content is scored to produce cognitive state information, and the vehicle is manipulated based on communication of the cognitive state information to a component of the vehicle.

The live streaming and image analysis 800 can be facilitated by a video capture device, a local server, a remote server, semiconductor-based logic, and so on. The streaming can be live streaming and can include cognitive state analysis, cognitive state event signature analysis, etc. Live streaming video is an example of one-to-many social media, where video can be sent over a computer network such as the Internet from one person to a plurality of people using a social media app and/or platform. Live streaming is one of numerous popular techniques used by people who want to disseminate ideas, send information, provide entertainment, and share experiences, and so on. Some of the live streams, such as webcasts, online classes, sporting events, news, computer gaming, or video conferences can be scheduled, while others can be impromptu streams that are broadcast as needed or when desired. Examples of impromptu live stream videos can range from individuals simply wanting to share experiences with their social media followers, to live coverage of breaking news, emergencies, or natural disasters. The latter coverage is known as mobile journalism, or "mojo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 800 shows a user 810 broadcasting a video live stream and an audio live stream to one or more people as shown by a first person 850, a second person 860, and a third person 870. A portable, network-enabled, electronic device 820 can be coupled to a front-side camera 822. The portable electronic device 820 can be a smartphone, a PDA, a tablet, a laptop computer, and so on. The camera 822 coupled to the device 820 can have a line-of-sight view 824 to the user 810 and can capture video of the user 810. The portable electronic device 820 can be coupled to a microphone (not shown). The microphone can capture voice data 828 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation machine 840 using a network link 826 to the network 830. The network link can be a wireless link, a wired link, and so on. The analysis machine 840 can recommend to the user 810 an app and/or platform that can be supported by the server and can be used to provide a video live stream, an audio live stream, or both a video live stream and an audio live stream to one or more followers of the user 810.

In the example 800, the user 810 has four followers: a first person 850, a second person 860, a third person 870, and a fourth person 880. Each follower has a line-of-sight view to a video screen on a portable, networked electronic device. In other embodiments, one or more followers follow the user 810 using any other networked electronic device, including a computer. In the example 800, a first person 850 has a line-of-sight view 852 to the video screen of a device 854; a second person 860 has a line-of-sight view 862 to the video screen of a device 864, a third person 870 has a line-of-sight view 872 to the video screen of a device 874, and a fourth person 880 has a line-of-sight view 882 to the video screen of a device 884. The device 874 can also capture audio data 878 from the third person 870, and the device 884 can further capture audio data 888 from the fourth person 880. The portable electronic devices 854, 864, 874, and 884 can each be a smartphone, a PDA, a tablet, and so on. Each portable device can receive the video stream and the audio stream being broadcast by the user 810 through the network 830 using the app and/or platform that can be recommended by the analysis or recommendation machine 840. The network can include the Internet, a computer network, a cellular network, and the like. The device 854 can receive a video stream and an audio stream using the network link 856, the device 864 can receive a video stream and an audio stream using the network link 866, the device 874 can receive a video stream and an audio stream using the network link 876, the device 884 can receive a video stream and an audio stream using the network link 886, and so on. The network link can be a wireless link, a wired link, a hybrid link, and the like. Depending on the app and/or platform that can be recommended by the analysis machine 840, one or more followers, such as the followers shown 850, 860, 870, and 880, can reply to, comment on, or otherwise provide feedback to the user 810 using their respective devices 854, 864, 874, and 884.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occlude or obscure the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g., smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g., television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of a specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques for counting occurrences of gradient orientation can be used, including edge orientation histograms, scale-invariant feature transformation descriptors, etc. The AU recognition tasks can also be performed using Local Binary Patterns (LBPs) and Local Gabor Binary Patterns (LGBPs). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 9:
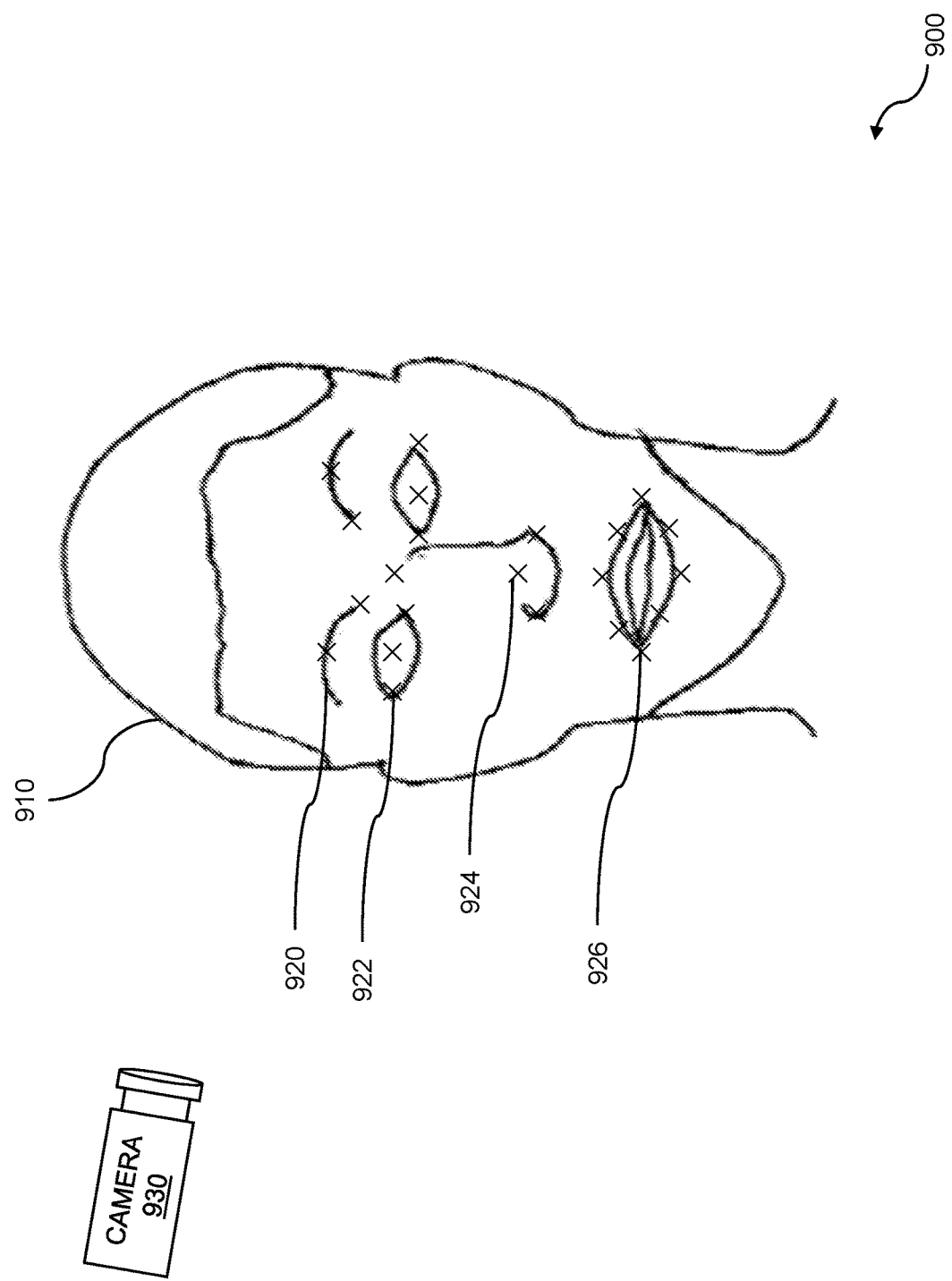
FIG. 9 shows example facial data collection including landmarks.

FIG. 9 shows example facial data collection including landmarks 900. The analysis of landmarks can be accomplished using logic such as convolutional processing logic encoded in a semiconductor chip. The convolutional processing logic can accomplish image analysis for facial evaluation in vehicles. Pixels within an image of a person in a vehicle are analyzed, where the analysis identifies a facial portion of the person. One or more facial expressions are identified based on the facial portion. The one or more facial expressions are classified for cognitive response content, and the cognitive response content is scored to produce cognitive state information for the person. The vehicle is manipulated based on communication of the cognitive state information to a component of the vehicle.

A face 910 can be observed using a camera 930 in order to collect facial data that includes facial landmarks. The facial data can be collected from a plurality of people using one or more of a variety of cameras. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend, for example, on the position of the camera 930 relative to the face 910, the number of cameras used, the illumination of the face, etc. For example, if the face 910 is poorly lit or over-exposed (e.g. in an area of bright light), the processing of the facial data to identify facial landmarks might be rendered more difficult. In another example, the camera 930 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 920, an outer eye edge 922, a nose 924, a corner of a mouth 926, and so on. Any number of facial landmarks can be identified from the facial data that is captured. The facial landmarks that are identified can be analyzed to identify facial action units. For example, the action units that can be identified can include AU02 outer brow raiser, AU14 dimpler, AU17 chin raiser, and so on. Any number of action units can be identified. The action units can be used alone and/or in combination to infer one or more cognitive states and emotions. A similar process can be applied to gesture analysis (e.g. hand gestures) with all of the analysis being accomplished or augmented by semiconductor-based logic.

Figure 10:
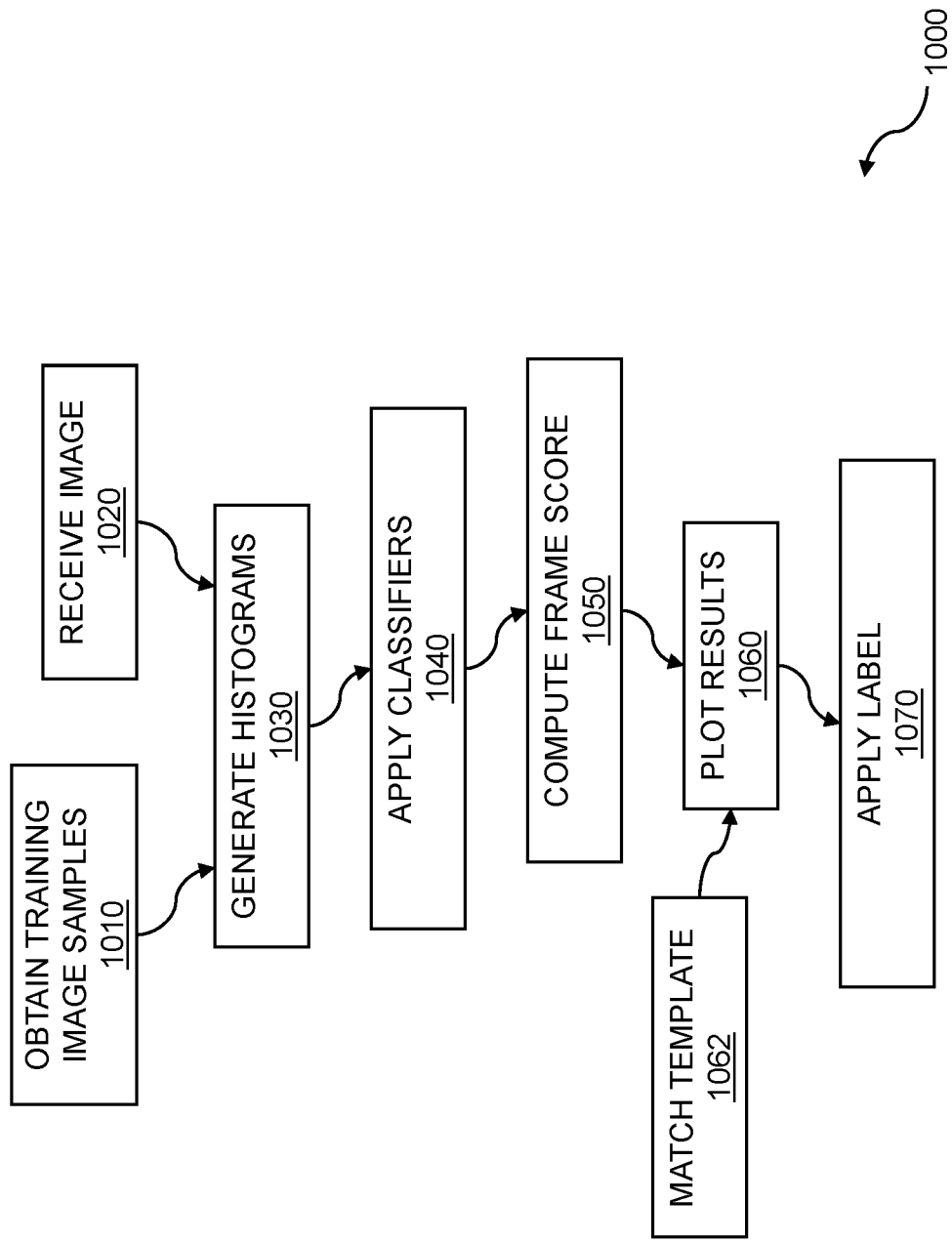
FIG. 10 is a flow diagram for detecting facial expressions.

FIG. 10 is a flow diagram for detecting facial expressions. This flow, or portions thereof, can be implemented in semiconductor logic. The flow 1000 can be used to automatically detect a wide range of facial expressions. A facial expression can produce strong cognitive signals that can indicate valence and discrete cognitive, mental, or emotional states. The discrete cognitive, mental, or emotional states can include contempt, doubt, defiance, happiness, fear, anxiety, and so on. The detection of facial expressions can be based on the location of facial landmarks or regions. The detection of facial expressions can be based on analyzing pixels within an image of a person in a vehicle, where the analysis identifies a facial portion of the person. The facial expressions can be identified based on the facial portion, and the facial expressions can be classified for cognitive response content. The cognitive response content can be scored to produce cognitive state information for the person, and a vehicle can be manipulated vehicle based on communication of the cognitive state information to a component of the vehicle. The detection of facial expressions can be based on determination of action units (AUs) where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1000 begins by obtaining training image samples 1010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, such as the camera 930 from FIG. 9, for example. The flow 1000 continues with receiving an image 1020. The image can be received from the camera 930. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. For example, the manipulated image and a flipped or mirrored version of the manipulated image can be analyzed alone and/or in combination to improve analysis. The flow 1000 continues with generating histograms 1030 for the training images and the one or more versions of the received image. The histograms can be generated for one or more versions of the manipulated received image. The histograms can be based on a HoG or another histogram. As described above, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example.

The flow 1000 continues with applying classifiers 1040 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. For example, the classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1000 continues with computing a frame score 1050. The score computed for an image, where the image can be a frame from a video, can be used to determine the presence of a facial expression in the image or video frame. The score can be based on one or more versions of the image 1020 or manipulated image. For example, the score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

Figure 11:
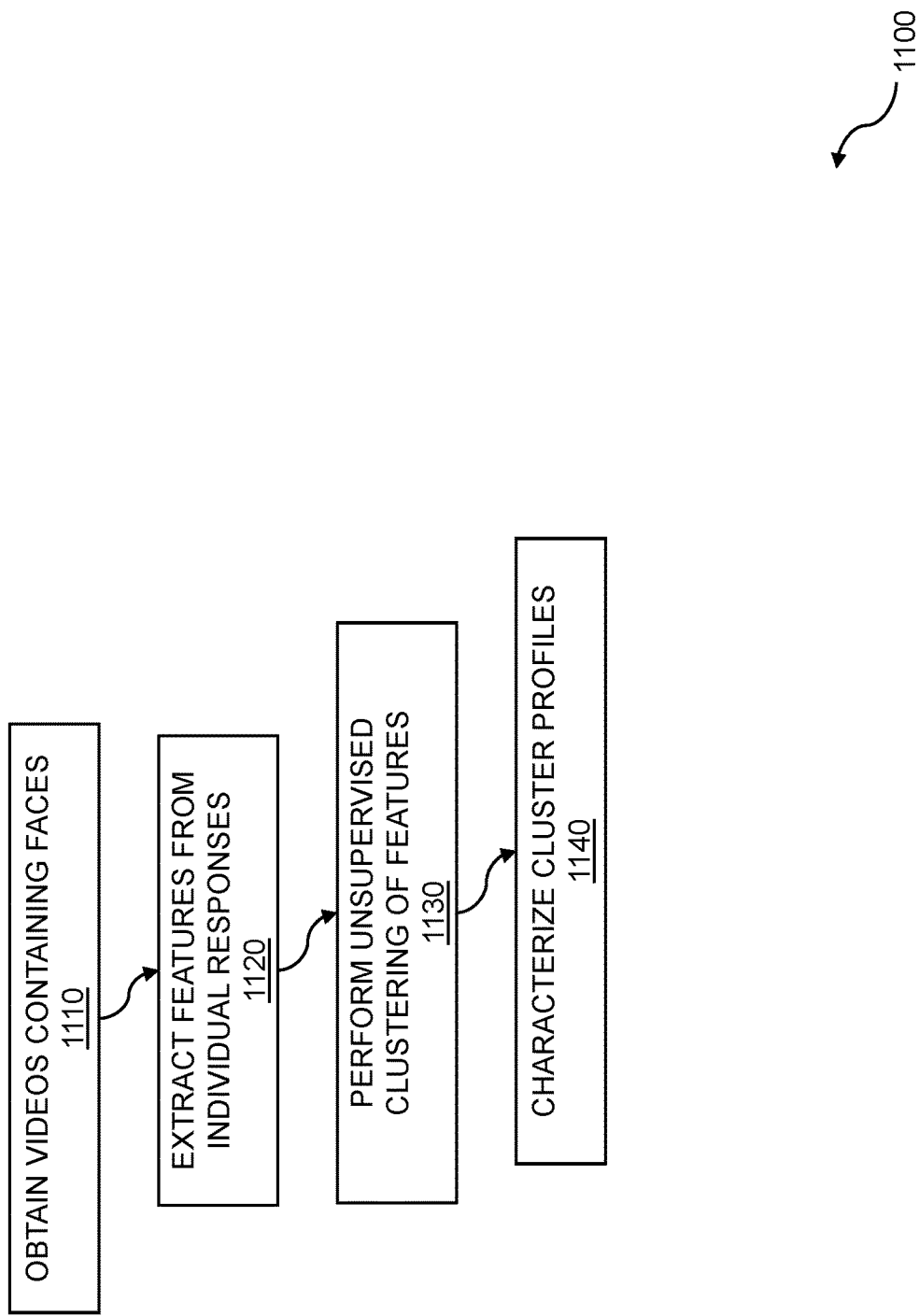
FIG. 11 is a flow diagram for the large-scale clustering of facial events.

The flow 1000 continues with plotting results 1060. The results that are plotted can include one or more scores for one or more frames computed over a given time t. For example, the plotted results can include classifier probability results from analysis of HoGs for a sequence of images and video frames. The plotted results can be matched with a template 1062. The template can be temporal and can be represented by a centered box function or another function. A best fit with one or more templates can be found by computing a minimum error. Other best-fit techniques can include polynomial curve fitting, geometric curve fitting, and so on. The flow 1000 continues with applying a label 1070. The label can be used to indicate that a particular facial expression has been detected in the one or more images or video frames which constitute the image that was received 1020. For example, the label can be used to indicate that any of a range of facial expressions has been detected, including a smile, an asymmetric smile, a frown, and so on. Various steps in the flow 1000 may be changed in order, repeated, omitted, or the like without departing from the disclosed concepts. Various embodiments of the flow 1000 can be included in a computer program product embodied in a non-transitory computer readable medium that includes code executable by one or more processors. Various embodiments of the flow 1000, or portions thereof, can be included on a semiconductor chip and implemented in special purpose logic, programmable logic, and so on FIG. 11 is a flow diagram for the large-scale clustering of facial events. The clustering and evaluation of facial events can be augmented using semiconductor-based logic. As discussed above, collection and evaluation of data such as facial video data from one or more people can include a web-based framework. The web-based framework can be used to collect facial video data from large numbers of people located over a wide geographic area, or one or more people in a vehicle. The web-based framework can include an opt-in feature that allows people to agree to facial data collection. The web-based framework can be used to render and display data to one or more people and can collect data from the one or more people. In a usage example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt in to the video data collection. The video event can be a commercial, a political ad, an educational segment, and so on. In embodiments, the large-scale clustering of facial events can be based on image analysis using a semiconductor processor. The image analysis, which can include convolutional processing, can be used for facial evaluation in vehicles.

The flow 1100 begins with obtaining videos containing faces 1110. The videos can be obtained using one or more cameras, where the cameras can include a webcam coupled to one or more devices employed by the one or more people using the web-based framework. The flow 1100 continues with extracting features from the individual responses 1120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1100 continues with performing unsupervised clustering of features 1130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1100 continues with characterizing cluster profiles 1140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. For example, the number of smiles resulting from people viewing a humorous video can be compared to various demographic groups, where the groups can be formed based on geographic location, age, ethnicity, gender, and so on.

Figure 12:
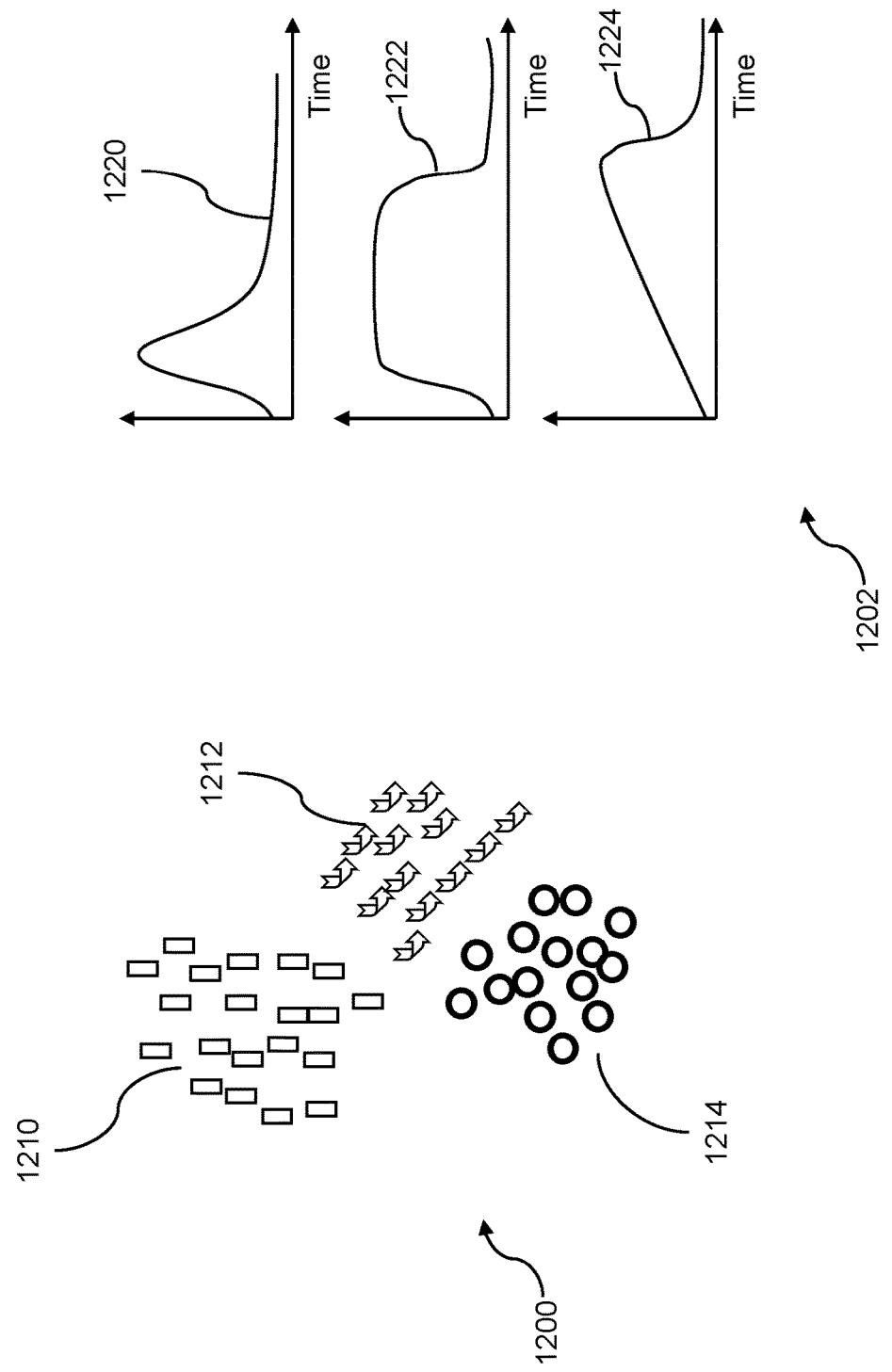
FIG. 12 shows example unsupervised clustering of features and characterizations of cluster profiles.

FIG. 12 shows example unsupervised clustering of features and characterization of cluster profiles. The unsupervised clustering and the characterization of cluster profiles can be based on image analysis, where the image analysis uses a semiconductor processor for facial evaluation in vehicles. Features including samples of data such as facial data, audio data, physiological data, and so on, can be clustered using unsupervised clustering. Various clusters can be formed, where the clusters include similar groupings of data observations such as facial data observations. The example 1200 shows three clusters 1210, 1212, and 1214. The clusters can be based on video collected from people who have opted in to video collection. When the collected data is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1202 can be generated based on the clusters that can be formed from unsupervised clustering, with time shown on the x-axis and intensity or frequency shown on the y-axis. The cluster profiles can be based on captured facial data including facial expressions, for example. The cluster profile 1220 can be based on the cluster 1210, the cluster profile 1222 can be based on the cluster 1212, and the cluster profile 1224 can be based on the cluster 1214. The cluster profiles 1220, 1222, and 1224 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 13A:
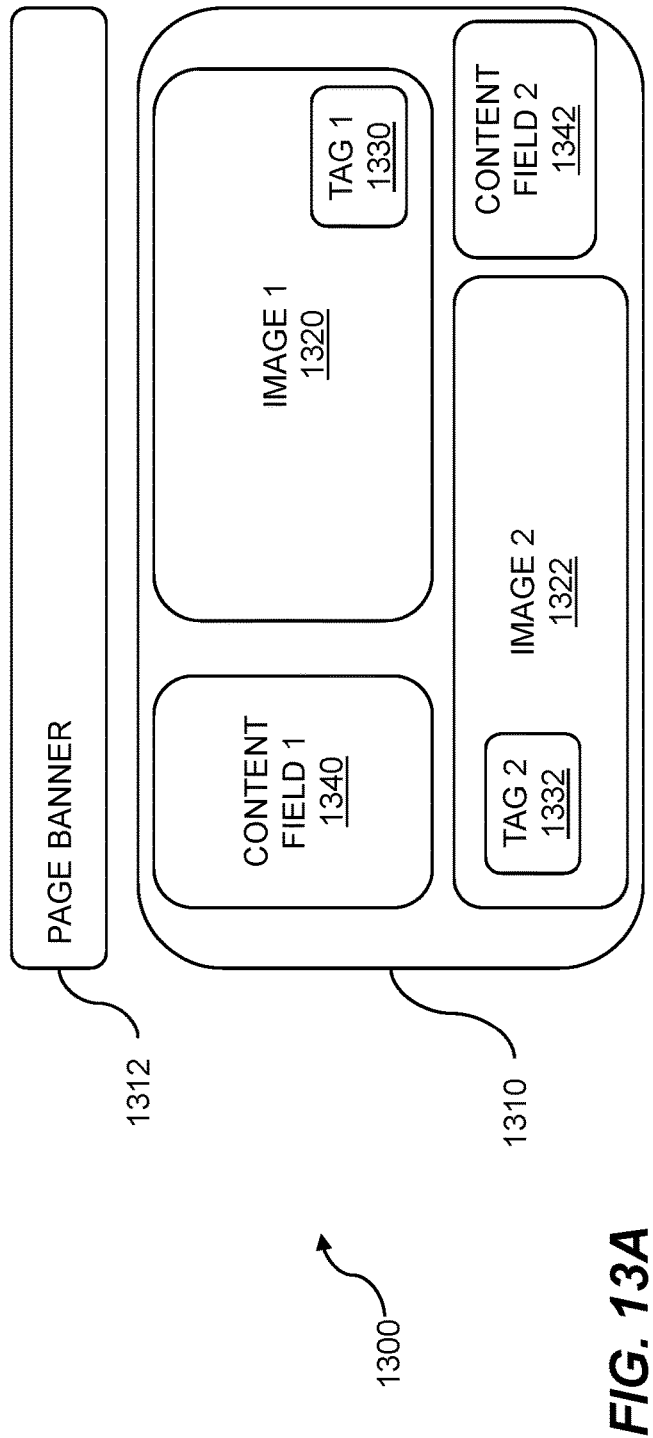
FIG. 13A shows example tags embedded in a webpage.

FIG. 13A shows example tags embedded in a webpage. Once a tag is detected, semiconductor-based logic can be used for convolutional processing for facial evaluation in vehicles. The facial evaluation can include evaluating facial expressions. The facial expressions can be evaluated by analyzing pixels within an image of a person in a vehicle. The facial expressions can be classified for cognitive response content, and the cognitive response content can be scored. A vehicle can be manipulated based on communication of the cognitive state information to a component of the vehicle. A webpage 1300 can include a page body 1310, a page banner 1312, and so on. The page body can include one or more objects, where the objects can include text, images, videos, audio, and so on. The example page body 1310 shown includes a first image, image 1 1320; a second image, image 2 1322; a first content field, content field 1 1340; and a second content field, content field 2 1342. In practice, the page body 1310 can contain any number of images and content fields, and can include one or more videos, one or more audio presentations, and so on. The page body can include embedded tags, such as tag 1 1330 and tag 2 1332. In the example shown, tag 1 1330 is embedded in image 1 1320, and tag 2 1332 is embedded in image 2 1322. In embodiments, any number of tags can be embedded. Tags can also be embedded in content fields, in videos, in audio presentations, etc. When a user mouses over a tag or clicks on an object associated with a tag, the tag can be invoked. For example, when the user mouses over tag 1 1330, tag 1 1330 can then be invoked. Invoking tag 1 1330 can include enabling a camera coupled to a user's device and capturing one or more images of the user as the user views a media presentation (or digital experience). In a similar manner, when the user mouses over tag 2 1332, tag 2 1332 can be invoked. Invoking tag 2 1332 can also include enabling the camera and capturing images of the user. In other embodiments, other actions are taken based on invocation of the one or more tags. For example, invoking an embedded tag can initiate an analysis technique, post to social media, award the user a coupon or another prize, initiate cognitive state analysis, perform emotion analysis, and so on.

Figure 13B:
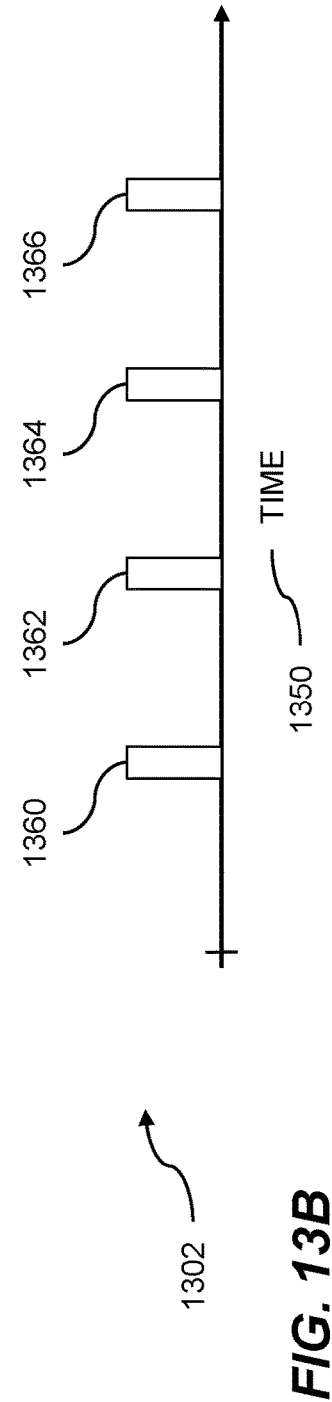
FIG. 13B shows an example of invoking tags to collect images.

FIG. 13B shows an example of invoking tags to collect images. As stated above, a media presentation can include a video, a webpage, and so on. A video 1302 can include one or more embedded tags, such as a tag 1360, another tag 1362, a third tag 1364, a fourth tag 1366, and so on. In practice, any number of tags can be included in the media presentation. The one or more tags can be invoked during the media presentation. The collection of the invoked tags can occur over time, as represented by a timeline 1350. When a tag is encountered in the media presentation, the tag can be invoked. For example, when the tag 1360 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled, and one or more images of the user can be captured. If the user has not agreed to participate in the study and has not indicated an opt-in, then invoking the tag 1360 does not enable the camera nor capture images of the user during the media presentation. The user can indicate an opt-in for certain types of participation, where opting-in can be dependent on specific content in the media presentation. For example, the user could opt in to participation in a study of political campaign messages and not opt in for a particular advertisement study. In this case, tags that are related to political campaign messages and that enable the camera and image capture when invoked would be embedded in the media presentation. However, tags embedded in the media presentation that are related to advertisements would not enable the camera when invoked. Various other situations of tag invocation are possible.

Figure 14:
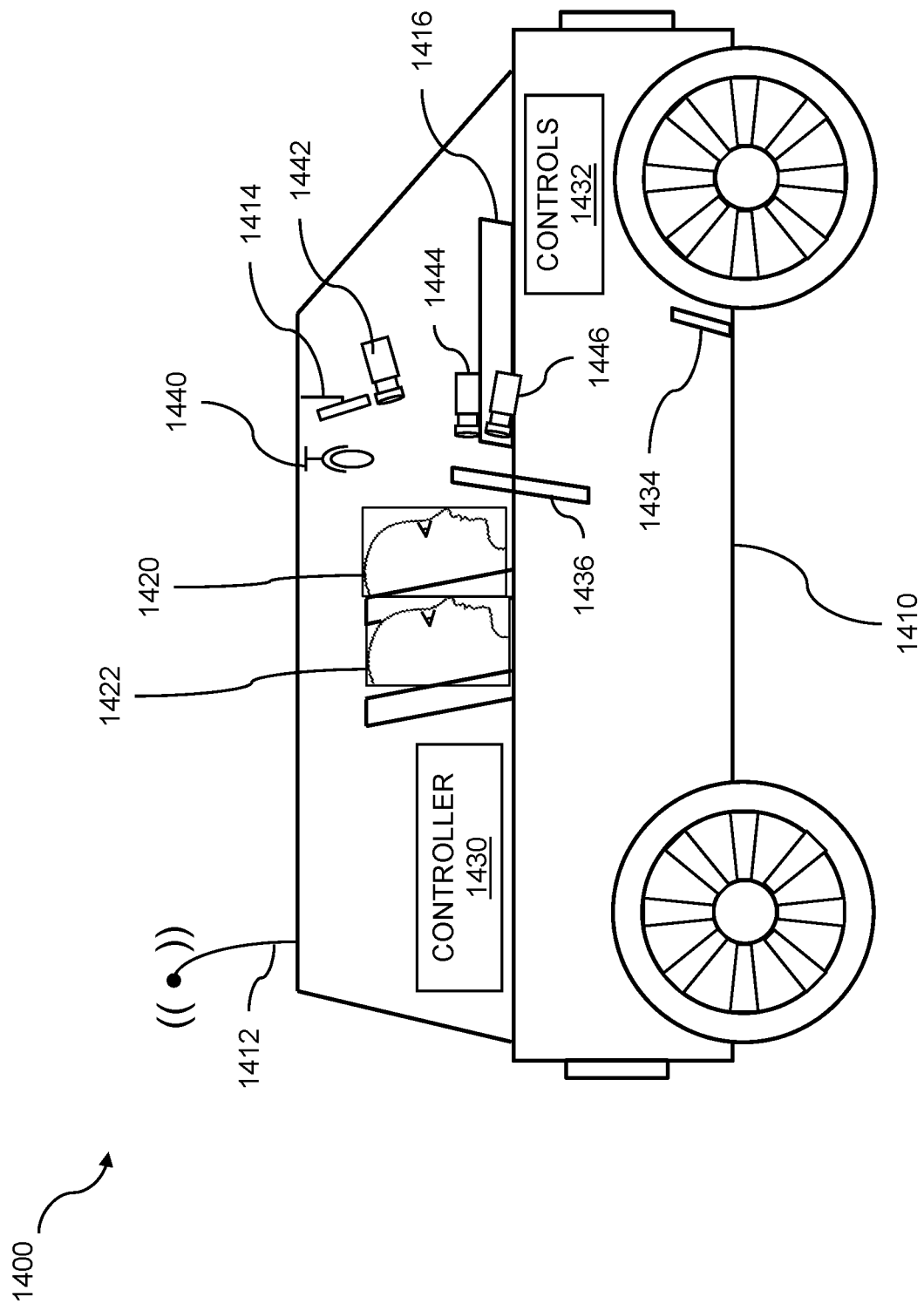
FIG. 14 is a system diagram for an interior of a vehicle.

FIG. 14 is a system diagram for an interior of a vehicle 1400. Vehicle manipulation can be based on cognitive state engineering. Data including video data, facial data, audio data, voice data, physiological data, and so on can be collected from a person in a vehicle. The images or other data can be analyzed based on convolutional processing to determine cognitive state. Pixels within an image of a person in a vehicle are analyzed to identify a facial portion of the person. Facial expressions are identified based on the facial portion, and the facial expressions are classified for cognitive response content. The cognitive response content is scored to produce cognitive state information, and the vehicle is manipulated based on communication of the cognitive state information to a component of the vehicle. One or more occupants of a vehicle 1410, such as occupants 1420 and 1422, can be observed using a microphone 1440, one or more cameras 1442, 1444, or 1446, and other audio and image capture techniques. The image data can include video data. The video data and the audio data can include cognitive state data, where the cognitive state data can include facial data, voice data, physiological data, and the like. The occupant can be a driver 1420 of the vehicle 1410, a passenger 1422 within the vehicle, and so on.

The cameras or imaging devices that can be used to obtain images including facial data from the occupants of the vehicle 1410 can be positioned to capture the face of the vehicle operator, the face of a vehicle passenger, multiple views of the faces of occupants of the vehicle, and so on. The cameras can be located near a rear-view mirror 1414 such as camera 1442, positioned near or on a dashboard 1416 such as camera 1444, positioned within the dashboard such as camera 1446, and so on. The microphone 1440, or audio capture device, can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 1410 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 1410 can include standard controls such as a steering wheel 1436, a throttle control (not shown), a brake 1434, and so on. The interior of the vehicle can include other controls 1432 such as controls for seats, mirrors, climate controls, audio systems, etc. The controls 1432 of the vehicle 1410 can be controlled by a controller 1430. The controller 1430 can control the vehicle 1410 in various manners such as autonomously, semi-autonomously, assertively to a vehicle occupant 1420 or 1422, etc. In embodiments, the controller provides vehicle control or manipulation techniques, assistance, etc. The controller 1430 can receive instructions via an antenna 1412 or using other wireless techniques. The controller 1430 can be preprogrammed to cause the vehicle to follow a specific route. The specific route that the vehicle is programmed to follow can be based on the cognitive state of the vehicle occupant. The specific route can be chosen based on lowest stress, least traffic, most scenic view, shortest route, and so on.

Figure 15:
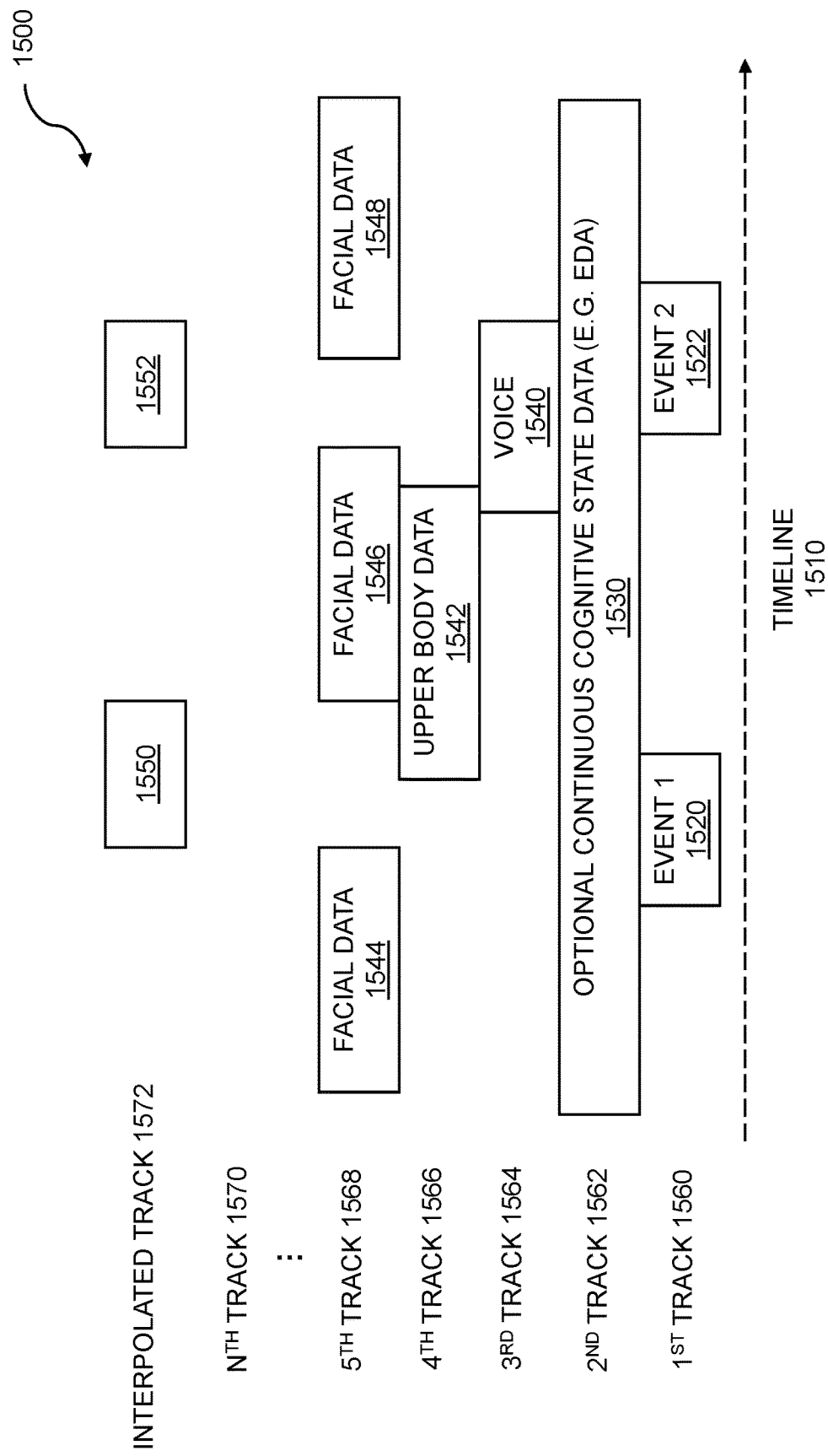
FIG. 15 is a timeline with information tracks relating to cognitive states.

FIG. 15 is a timeline with information tracks 1500 relating to cognitive states. A timeline can show one or more cognitive states that can be experienced by an individual. The timeline can be based analysis performed on a chip containing convolutional processing logic within a semiconductor chip. Pixels within an image of a person in a vehicle are analyzed, where the analysis identifies a facial portion of the person. Facial expressions are identified based on the facial portion, and the facial expressions are classified for cognitive response content. The cognitive response content is scored to produce cognitive state information for the person, and the vehicle is manipulated based on communication of the cognitive state information to a component of the vehicle. The timeline 1510 with information tracks 1500 relates to various cognitive states. A first track 1560 shows events that, in embodiments, are related to use of a computer by the individual. A first event 1520 can indicate an action that the individual took (such as launching an application); an action initiated by the computer (such as the presentation of a dialog box); an external event (such as a new global positioning system (GPS) coordinate); or another event such as receiving an email, a phone call, a text message, or any other type of event. In some embodiments, a photograph can be used to document an event or simply to save contextual information in the first track 1560. A second event 1522 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 1562 can include continuously collected cognitive state data such as electrodermal activity data 1530. A third track 1564 can include voice data 1540. The upper body data, such as upper torso data, can be collected intermittently when the individual is looking toward a camera. The voice data 1540 can include one or more still photographs, videos, or infrared images which can be collected when the user looks in the direction of the camera. A fourth track 1566 also can include upper body data that is collected either intermittently or continuously by a second imaging device. The upper body data 1542 can include one or more still photographs, videos, infrared images, or abstracted caricatures which can be collected when the user looks in the direction of that camera. A fifth track 1568 can include facial data that is collected from a third camera, such as the webcam. In the example shown, the fifth track 1568 includes first facial data 1544, second facial data 1546, and third facial data 1548, which can be any type of facial data including data that can be used for determining cognitive state information. Any number of samples of facial data can be collected in any track. The cognitive state data from the various tracks can be collected simultaneously, collected on one track exclusive of other tracks, collected where cognitive state data overlaps between the tracks, and so on. When cognitive state data from multiple tracks overlap, one track's data can take precedence over another track or the data from the multiple tracks can be combined.

Additional tracks, through the $n^{th}$ track 1570, of cognitive state data of any type can be collected. The additional tracks 1570 can be collected on a continuous or on an intermittent basis. The intermittent basis can be either occasional or periodic. Analysis can further comprise interpolating cognitive state data when the cognitive state data collected is intermittent, and/or imputing additional cognitive state data where the cognitive state data is missing. One or more interpolated tracks 1572 can be included and can be associated with cognitive state data that is collected on an intermittent basis, such as the facial data of the fifth track 1568. Interpolated data 1550 and further interpolated data 1552 can contain interpolations of the facial data of the fifth track 1568 for the time periods where no facial data was collected in that track. Other embodiments interpolate data for periods where no track includes facial data. In other embodiments, analysis includes interpolating cognitive state analysis when the cognitive state data collected is intermittent.

The cognitive state data, such as the continuous cognitive state data 1530 and/or any of the collected voice data 1540 and upper body data 1542, and/or facial data 1544, 1546, and 1548, can be tagged. The tags can include metadata related to the cognitive state data, including, but not limited to, the device that collected the cognitive state data; the individual from whom the cognitive state data was collected; the task being performed by the individual; the media being viewed by the individual; and the location, environ-cognitive conditions, time, date, or any other contextual information. The tags can be used to locate pertinent cognitive state data; for example, the tags can be used to retrieve the cognitive state data from a database. The tags can be included with the cognitive state data that is sent over the internet to cloud or web-based storage and/or services. As such, the tags can be used locally on the machine where the cognitive state data was collected and/or remotely on a remote server or a cloud/web service.

Other tags can be related to the cognitive state data, which is data related to, attached to, indicative of, including, containing, etc., the cognitive state. Further embodiments can include tagging the cognitive state data with sensor data. The sensor data can be obtained from the vehicle occupant along with the video data or the audio data, instead of the video data or the audio data, etc. In embodiments, the sensor data can include one or more of vehicle temperature, outside temperature, time of day, level of daylight, weather conditions, headlight activation, windshield wiper activation, entertainment center selection, or entertainment center volume. Other sensor data can include physiological data related to one or more occupants of the vehicle. The physiological data can include heart rate, heart rate variability, electrodermal activity, acceleration, and the like. The tags can also be related to the cognitive state that can be determined by image-based analysis of the video, audio, or physiological data, or other techniques. In embodiments, the tags that can be applied can be based on one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 16:
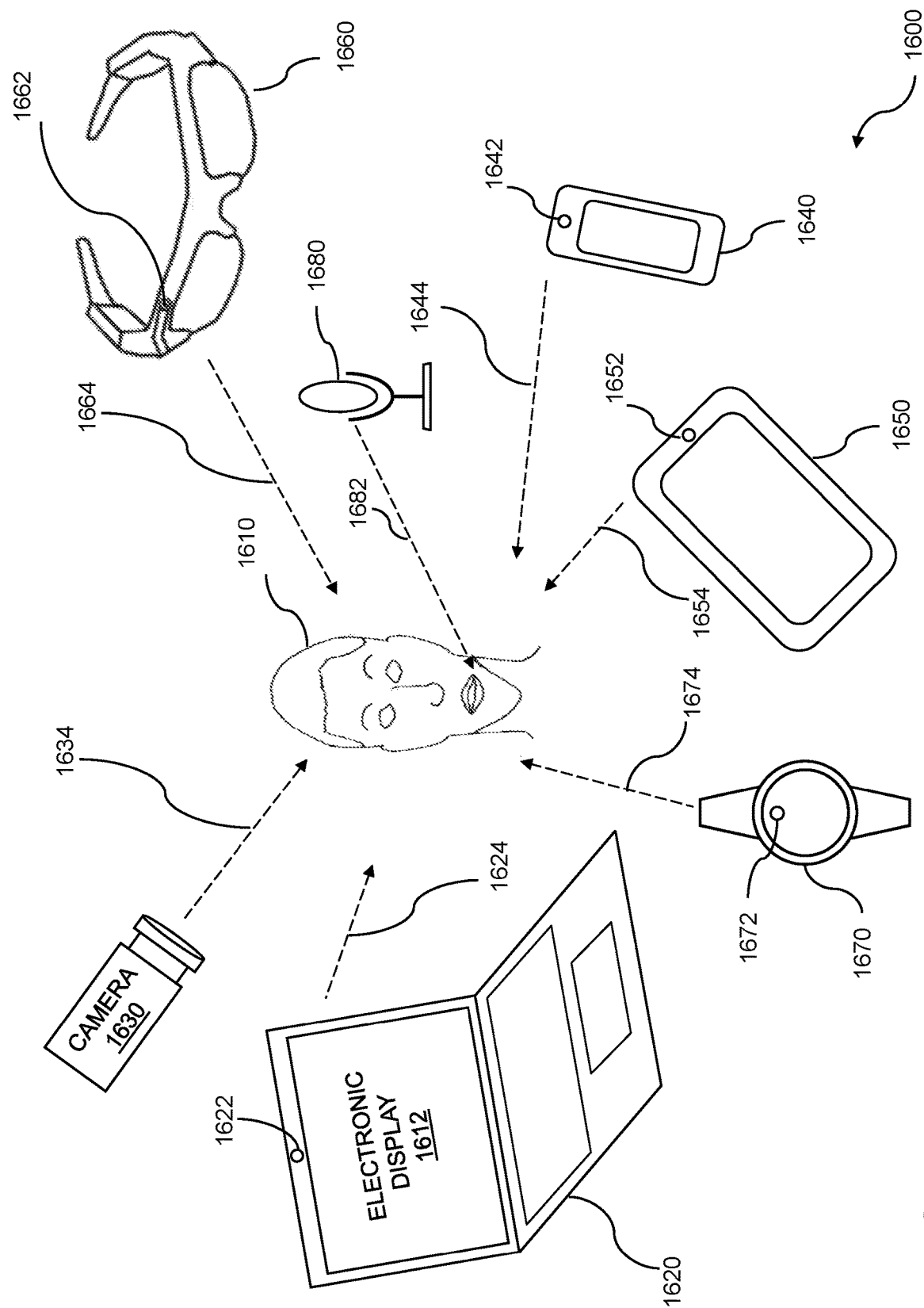
FIG. 16 illustrates example image and audio collection including multiple mobile devices.

FIG. 16 illustrates example image and audio collection including multiple mobile devices. Images, which can include facial or torso data, cognitive state data, audio data, and physiological data, can be collected using multiple mobile devices. The image data can be analyzed using convolutional processing. The convolutional processing can be applied to neural network training, where the neural network training can enable deep learning. The deep learning can enable image analysis for facial evaluation in vehicles. Images that include facial data are obtained for cognitive state analysis. An image of a person in a vehicle is evaluated, where the analysis identifies a facial portion of the person. The analysis can also identify a body portion such as a torso, an object within the vehicle, and so on. One or more facial expressions are identified based on the facial portion. The one or more facial expressions are classified for cognitive response content. The cognitive response content is scored to produce cognitive state information for the person. The vehicle is manipulated based on communication of the cognitive state information to a component of the vehicle. A cognitive state can include drowsiness, fatigue, distraction, impairment, sadness, stress, happiness, anger, frustration, confusion, disappointment, hesitation, human perception overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

In the diagram 1600, the multiple mobile devices can be used separately or in combination to collect video data, audio data, physiological data, or some or all of video data, audio data, and physiological data, on a user 1610. While one person is shown, the imaging, video data, audio data, or physiological data can be collected on multiple people. A user 1610 can be observed as she or he is performing a task, experiencing an event, viewing a media presentation, and so on. The user 1610 can be shown one or more media presentations, political presentations, social media, or another form of displayed media. The one or more media presentations can be shown to a plurality of people. The media presentations can be displayed on an electronic display 1612 or another display. The data collected on the user 1610 or on a plurality of users can be in the form of one or more videos, video frames, and still images; one or more audio channels, etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As noted before, video data and audio data can be collected on one or more users in substantially identical or different situations while viewing either a single media presentation or a plurality of presentations. The data collected on the user 1610 can be analyzed and viewed for a variety of purposes including expression analysis, cognitive state analysis, mental state analysis, emotional state analysis, and so on. The electronic display 1612 can be on a laptop computer 1620 as shown, a tablet computer 1650, a cell phone 1640, a television, a mobile monitor, or any other type of electronic device. In one embodiment, video data including expression data is collected on a mobile device such as a cell phone 1640, a tablet computer 1650, a laptop computer 1620, or a watch 1670. Similarly, the audio data including speech data and non-speech vocalizations can be collected on one or more of the mobile devices. Thus, the multiple sources can include at least one mobile device, such as a phone 1640 or a tablet 1650, or a wearable device such as a watch 1670 or glasses 1660. A mobile device can include a front-side camera and/or a back-side camera that can be used to collect expression data. A mobile device can include a microphone, audio transducer, or other audio capture apparatus that can be used to capture the speech and non-speech vocalizations. Sources of expression data can include a webcam 1622, a phone camera 1642, a tablet camera 1652, a wearable camera 1662, and a mobile camera 1630. A wearable camera can comprise various camera devices, such as a watch camera 1672. Sources of audio data 1682 can include a microphone 1680.

As the user 1610 is monitored, the user might move due to the nature of the task, boredom, discomfort, distractions, or for another reason. As the user moves, the camera with a view of the user's face can be changed. Thus, as an example, if the user is looking in a first direction, the line of sight 1624 from the webcam 1622 is able to observe the user's face, but if the user is looking in a second direction, the line of sight 1634 from the mobile camera 1630 is able to observe the user's face. Furthermore, in other embodiments, if the user is looking in a third direction, the line of sight 1644 from the phone camera 1642 is able to observe the user's face, and if the user is looking in a fourth direction, the line of sight 1654 from the tablet camera 1652 is able to observe the user's face. If the user is looking in a fifth direction, the line of sight 1664 from the wearable camera 1662, which can be a device such as the glasses 1660 shown which can be worn by another user or an observer, is able to observe the user's face. If the user is looking in a sixth direction, the line of sight 1674 from the wearable watch-type device 1670, with a camera 1672 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1610 can also use a wearable device including a camera for gathering contextual information and/or collecting expression data on other users. Because the user 1610 can move her or his head, the facial data can be collected intermittently when she or he is looking in a direction of a camera. In some cases, multiple people can be included in the view from one or more cameras, and some embodiments include filtering out faces of one or more other people to determine whether the user 1610 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 17:
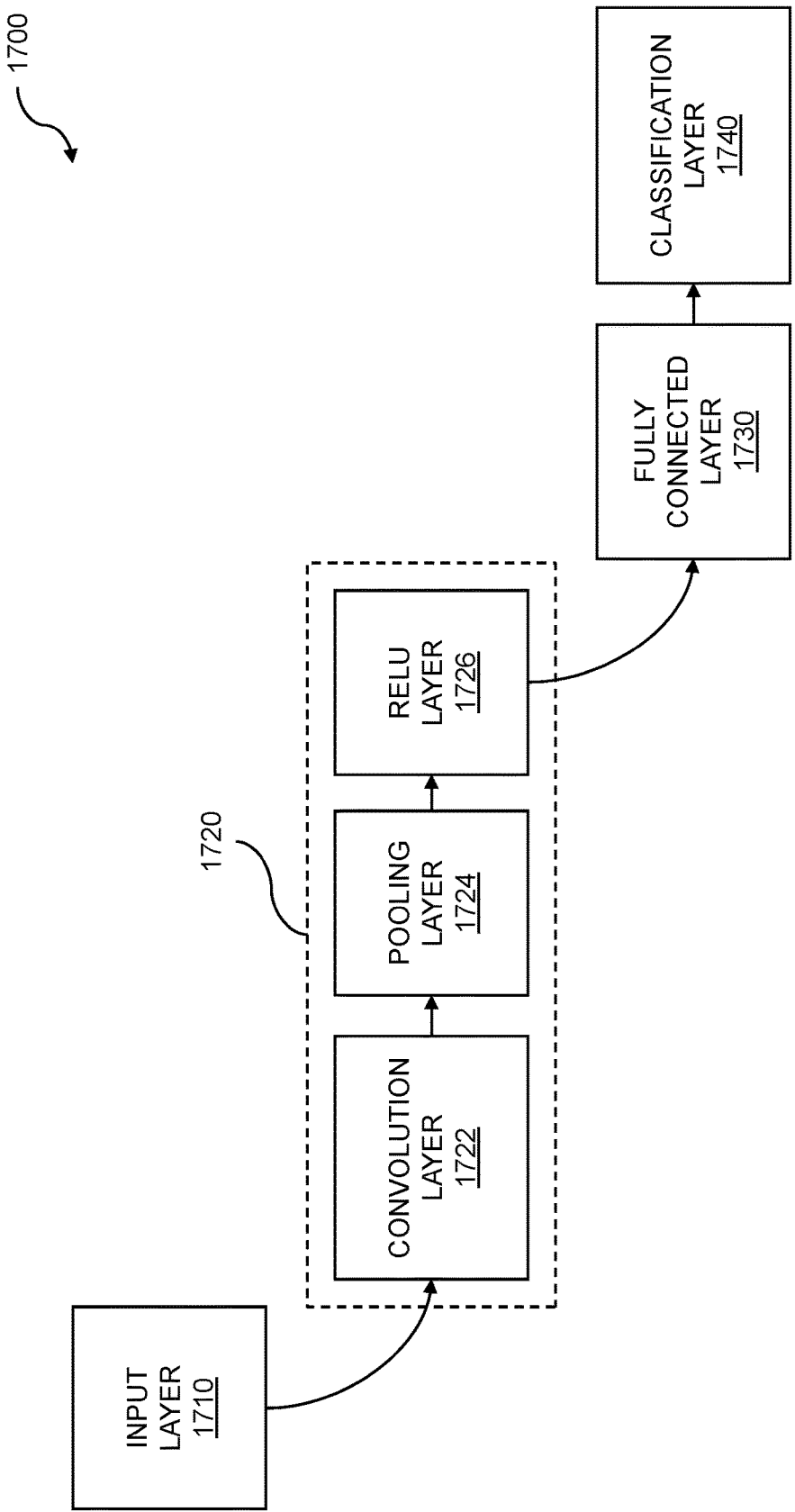
FIG. 17 is an example showing a convolutional neural network.

FIG. 17 is an example showing a convolutional neural network (CNN). A convolutional neural network, such as network 1700, can be used for various applications. The applications for which the CNN can be used can include deep learning, where the deep learning can be applied to convolutional processing. The convolutional processing supports image analysis using a semiconductor processor for facial evaluation in vehicles. Pixels within an image of a person in a vehicle are used to analyze a facial portion of the person. The image can include an image of a vehicle interior, where the image can be collected using various types of imaging devices. Other data such as audio data or physiological data can also be collected. One or more facial expressions are identified based on the facial portion. The one or more facial expressions are classified for cognitive response content. The cognitive response content is scored to produce cognitive state information for the person. The vehicle is manipulated based on communication of the cognitive state information to a component of the vehicle. A component of the vehicle can include adjusting vehicle climate control or audio selection, adjusting to traffic or weather, proposing an alternative route, and the like. The convolutional neural network can be applied to analysis tasks such as image analysis, cognitive state analysis, mental state analysis, mood analysis, emotional state analysis, and so on. The CNN can be applied to various tasks such as autonomous vehicle or semiautonomous vehicle manipulation, vehicle content recommendation, and the like. When the imaging and other data collected includes cognitive state data, the cognitive state data can include mental processes, where the mental processes can include attention, creativity, memory, perception, problem solving, thinking, use of language, or the like.

Analysis, including cognitive analysis, is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 17 is an example showing a convolutional neural network 1700. The convolutional neural network can be used for deep learning, where the deep learning can be applied to image analysis for human perception artificial intelligence. The deep learning system can be accomplished using a variety of networks. In embodiments, the deep learning can be performed using a convolution neural network. Other types of networks or neural networks can also be used. In other embodiments, the deep learning can be performed using a recurrent neural network. The deep learning can accomplish upper torso identification, facial recognition, analysis tasks, etc. The network includes an input layer 1710. The input layer 1710 receives image data. The image data can be input in a variety of formats, such as JPEG, TIFF, BMP, and GIF. Compressed image formats can be decompressed into arrays of pixels, wherein each pixel can include an RGB tuple. The input layer 1710 can then perform processing such as identifying boundaries of the face, identifying landmarks of the face, extracting features of the face, and/or rotating a face within the plurality of images.

The network includes a collection of intermediate layers 1720. The multilayered analysis engine can include a convolutional neural network. Thus, the intermediate layers can include a convolution layer 1722. The convolution layer 1722 can include multiple sublayers, including hidden layers, within it. The output of the convolution layer 1722 feeds into a pooling layer 1724. The pooling layer 1724 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 175-percent of the downstream node activations. The multilayered analysis engine can further include a max pooling layer 1724. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Unit (RELU) layer 1726. The output of the pooling layer 1724 can be input to the RELU layer 1726. In embodiments, the RELU layer implements an activation function such as $f(x)=\max(0,x)$, thus providing an activation with a threshold at zero. In some embodiments, the RELU layer 1726 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1722 and one or more hidden layers, and wherein the multilayered analysis engine can be used for emotional analysis.

The example 1700 includes a fully connected layer 1730. The fully connected layer 1730 processes each pixel/data point from the output of the collection of intermediate layers 1720. The fully connected layer 1730 takes all neurons in the previous layer and connects them to every single neuron it has. The output of the fully connected layer 1730 provides input to a classification layer 1740. The output of the classification layer 1740 provides a facial expression and/or cognitive state as its output. Thus, a multilayered analysis engine such as the one depicted in FIG. 17 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy; whether a voice is female, male, or robotic; whether a message is legitimate email or a "spam" message; and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, online or computational performance is the focus. Online performance includes finding a balance between exploration of new (uncharted) territory or spaces and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and the algorithm. Positive outcomes can include the person being more engaged, where engagement is based on affect, the person spending more time playing an online game or navigating a webpage, the person converting by buying a product or service, and so on. The reinforced learning can be based on exploring a solution space and adapting the model, algorithm, etc., which stem from outcomes of the exploration. When positive outcomes are encountered, the positive outcomes can be reinforced by changing weighting values within the model, algorithm, etc. Positive outcomes may result in increased weighting values. Negative outcomes can also be considered, where weighting values may be reduced or otherwise adjusted.

Figure 18:
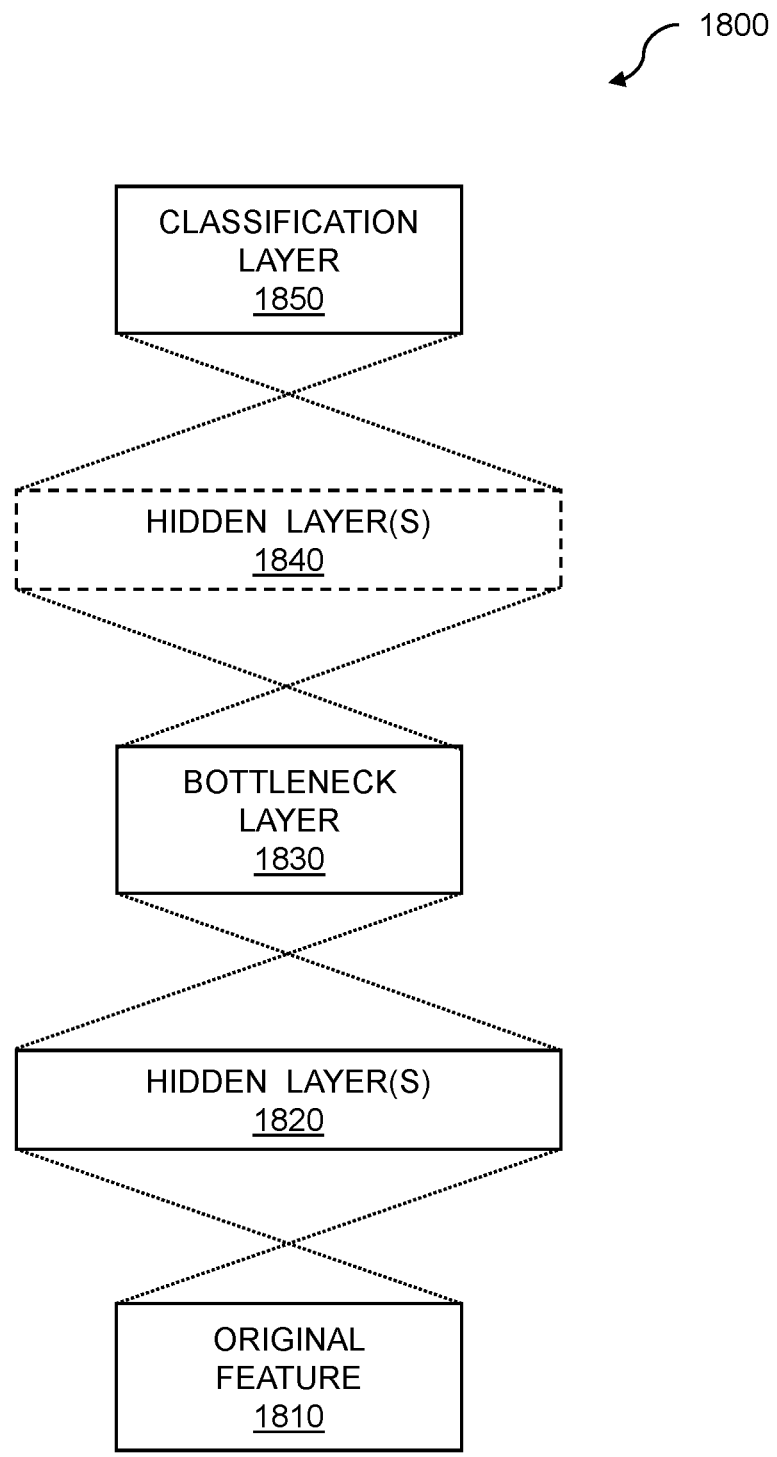
FIG. 18 illustrates a bottleneck layer within a deep learning environment.

FIG. 18 illustrates a bottleneck layer within a deep learning environment. A deep learning environment can be based on a neural network such as a deep neural network. The deep neural network comprises a plurality of layers such as input layers, output layers, convolution layers, activation layers, and so on. The plurality of layers in a deep neural network (DNN) can include a bottleneck layer. The bottleneck layer can be used for neural network training, where the training can be applied to analysis such as image analysis. The deep learning network can be implemented using a semiconductor chip for convolutional processing. A deep neural network can apply classifiers such as object classifiers, image classifiers, facial classifiers, audio classifiers, speech classifiers, physiological classifiers, and so on. The classifiers can be learned by analyzing one or more of cognitive states, cognitive load metrics, interaction metrics, etc. Pixels within an image of a person in a vehicle are analyzed to identify a facial portion of the person. Facial expressions associated with the person are identified based on the facial portion. The facial expressions are classified for cognitive response content. The cognitive response content is scored to produce cognitive state information for the person. Manipulation of the vehicle is enabled based on communication of the cognitive state information to a component of the vehicle.

Layers of a deep neural network can include a bottleneck layer 1800. A bottleneck layer can be used for a variety of applications such as identification of a facial portion, identification of an upper torso, facial recognition, voice recognition, emotional state recognition, and so on. The deep neural network in which the bottleneck layer is located can include a plurality of layers. The plurality of layers can include an original feature layer 1810. A feature such as an image feature can include points, edges, objects, boundaries between and among regions, properties, and so on. The deep neural network can include one or more hidden layers 1820. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1830. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 1840. The number of the hidden layers can include zero hidden layers, one hidden layer, a plurality of hidden layers, and so on. The hidden layers following the bottleneck layer can include more nodes than the bottleneck layer. The deep neural network can include a classification layer 1850. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 19:
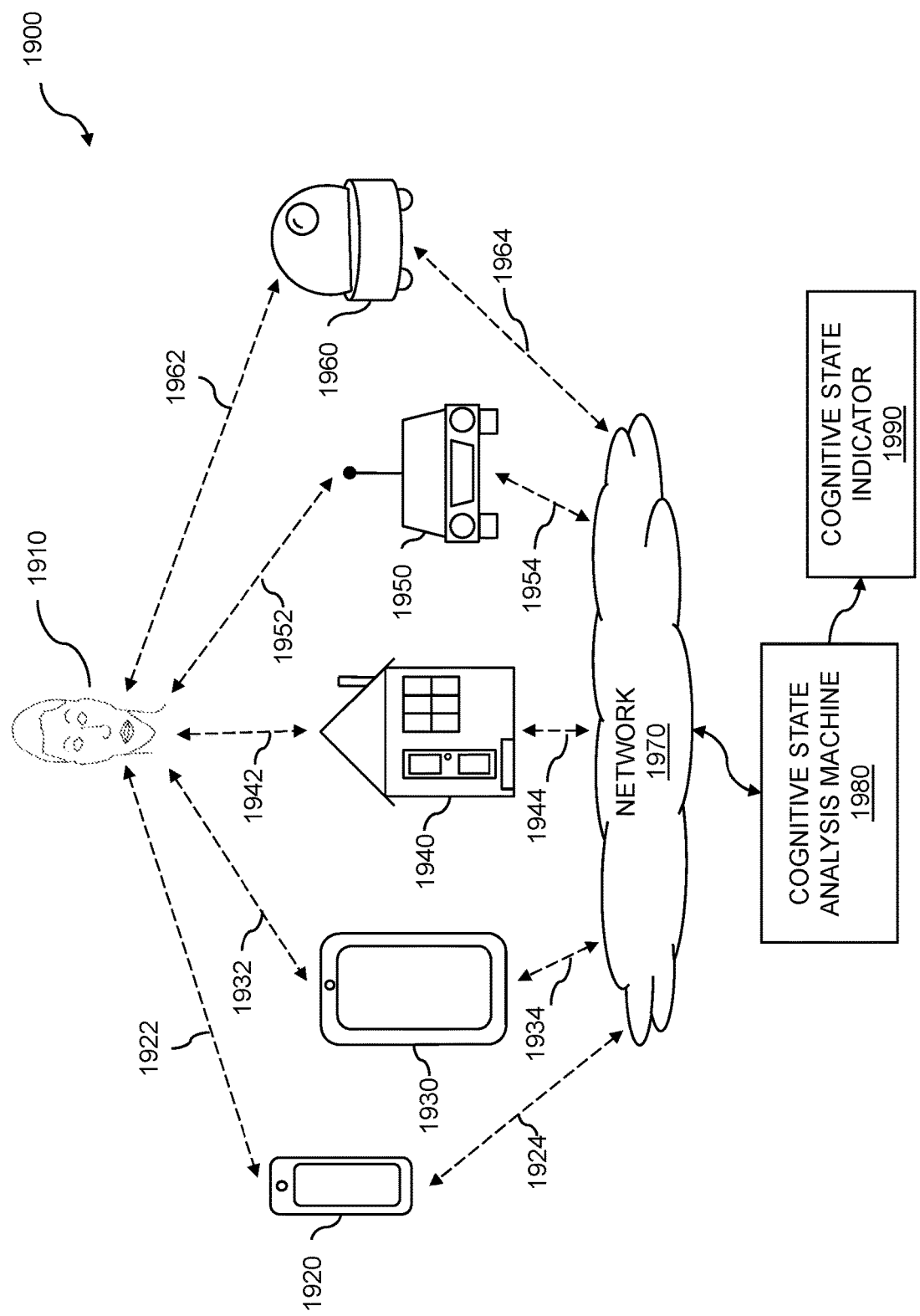
FIG. 19 shows data collection including devices and locations.

FIG. 19 shows data collection including devices and locations 1900. Data, including imaging, facial data, video data, audio data, and physio data can be obtained for analysis such as image analysis using a semiconductor processor. The semiconductor can be used for facial evaluation of one or more persons in vehicles. The imaging, audio, physio, and other data can be obtained from multiple devices, vehicles, and locations. Pixels within an image of a person in a vehicle are analyzed, where the analysis identifies a facial portion of the person. One or more facial expressions are identified based on the facial portion. The one or more facial expressions are classified for cognitive response content. The cognitive response content is evaluated to produce cognitive state information for the person. The vehicle is manipulated based on communication of the cognitive state information to a component of the vehicle.

The multiple mobile devices, vehicles, and locations 1900 can be used separately or in combination to collect imaging, video data, audio data, physio data, etc., on a user 1910. The imaging can include video data, where the video data can include upper torso data. Other data such as audio data, physiological data, and so on, can be collected on the user. While one person is shown, the video data, or other data, can be collected on multiple people. A user 1910 can be observed as she or he is performing a task, experiencing an event, viewing a media presentation, and so on. The user 1910 can be shown one or more media presentations, political presentations, social media, or another form of displayed media. The one or more media presentations can be shown to a plurality of people. The media presentations can be displayed on an electronic display coupled to a client device. The data collected on the user 1910 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1910 can be analyzed and viewed for a variety of purposes including body position or body language analysis, expression analysis, mental state analysis, cognitive state analysis, and so on. The electronic display can be on a smartphone 1920 as shown, a tablet computer 1930, a personal digital assistant, a television, a mobile monitor, or any other type of electronic device. In one embodiment, expression data is collected on a mobile device such as a cell phone 1920, a tablet computer 1930, a laptop computer, or a watch. Thus, the multiple sources can include at least one mobile device, such as a phone 1920 or a tablet 1930, or a wearable device such as a watch or glasses (not shown). A mobile device can include a front-side camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1910, data can be collected in a house 1940 using a web camera or the like; in a vehicle 1950 using a web camera, client device, etc.; by a social robot 1960, and so on.

As the user 1910 is monitored, the user 1910 might move due to the nature of the task, boredom, discomfort, distractions, or for another reason. As the user moves, the camera with a view of the user's face can be changed. Thus, as an example, if the user 1910 is looking in a first direction, the line of sight 1922 from the smartphone 1920 is able to observe the user's face, but if the user is looking in a second direction, the line of sight 1932 from the tablet 1930 is able to observe the user's face. Furthermore, in other embodiments, if the user is looking in a third direction, the line of sight 1942 from a camera in the house 1940 is able to observe the user's face, and if the user is looking in a fourth direction, the line of sight 1952 from the camera in the vehicle 1950 is able to observe the user's face. If the user is looking in a fifth direction, the line of sight 1962 from the social robot 1960 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1910 can also use a wearable device including a camera for gathering contextual information and/or collecting expression data on other users. Because the user 1910 can move her or his head, the facial data can be collected intermittently when she or he is looking in a direction of a camera. In some cases, multiple people can be included in the view from one or more cameras, and some embodiments include filtering out faces of one or more other people to determine whether the user 1910 is looking toward a camera. All or some of the expression data can be continuously or sporadically available from the various devices and other devices.

The captured video data can include cognitive content, such as facial expressions, etc., and can be transferred over a network 1970. The network can include the Internet or other computer network. The smartphone 1920 can share video using a link 1924, the tablet 1930 using a link 1934, the house 1940 using a link 1944, the vehicle 1950 using a link 1954, and the social robot 1960 using a link 1964. The links 1924, 1934, 1944, 1954, and 1964 can be wired, wireless, and hybrid links. The captured video data, including facial expressions, can be analyzed on a cognitive state analysis machine 1980, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 1990. The cognitive state indicator 1990 can indicate cognitive states, mental states, moods, emotions, etc. In embodiments, the cognitive state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 20:
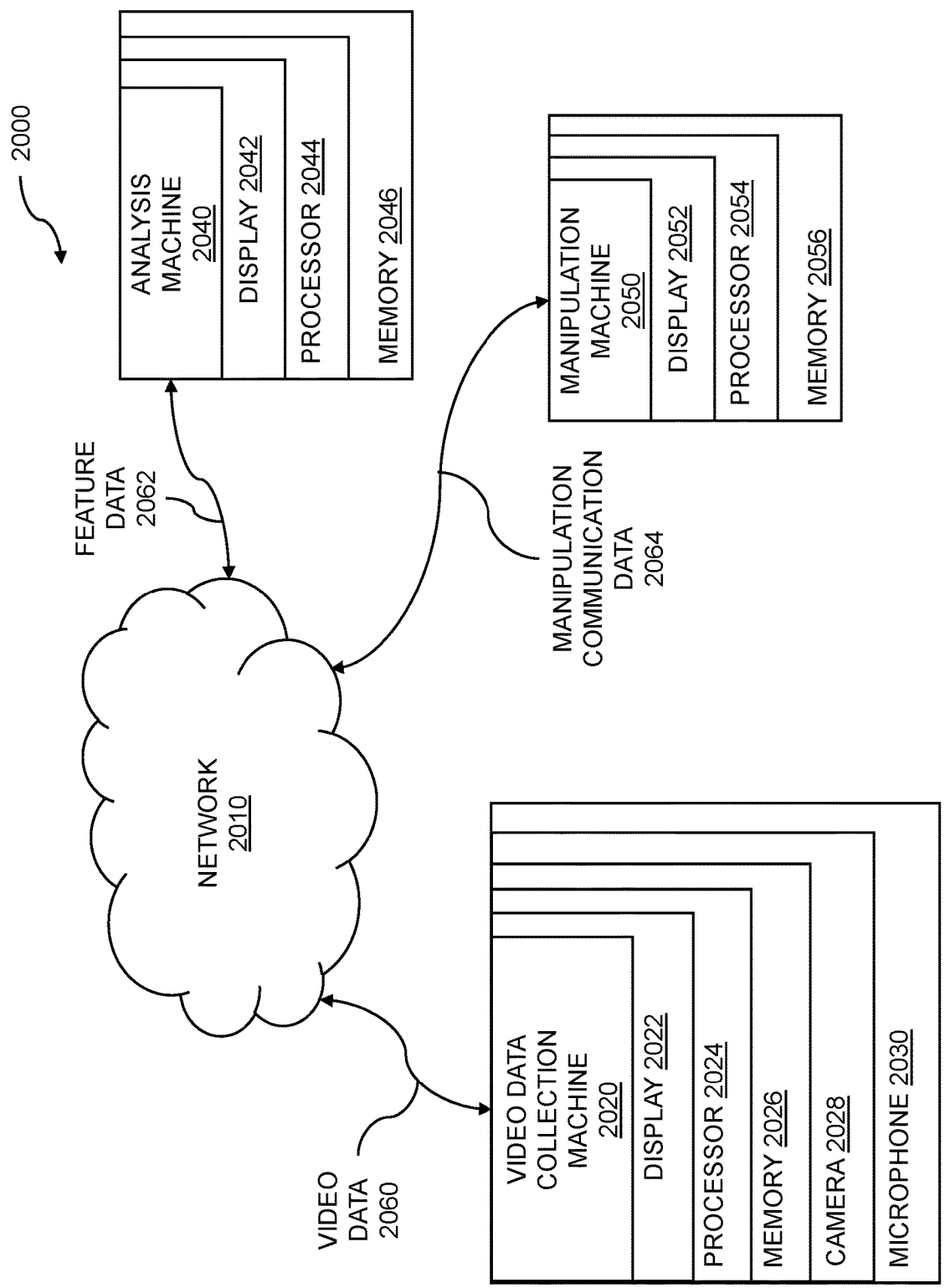
FIG. 20 is a system for cognitive state analysis.

FIG. 20 is a system for image and cognitive state analysis using a convolutional processing device. The convolutional processing device uses semiconductor-based logic to perform or augment the needed analysis. An example system 2000 is shown for cognitive state data collection and analysis. The analyzed cognitive state data is used for vehicle manipulation. The system 2000 can include a memory which stores instructions and one or more processors attached to the memory, wherein the one or more processors, when executing the instructions which are stored, are configured to: analyze pixels within an image of a person in a vehicle, wherein the analysis identifies a facial portion of the person; identify one or more facial expressions based on the facial portion; classify the one or more facial expressions for cognitive response content; evaluate the cognitive response content to produce cognitive state information for the person; and manipulate the vehicle based on communication of the cognitive state information to a component of the vehicle. In embodiments, the device updates a cognitive state profile the person associated with the facial portion. The cognitive state profile summarizes the cognitive state information of the individual. In some embodiments, an additional facial portion from an image of an additional person within the vehicle is evaluated, identified, classified, and scored to produce additional cognitive state information for the additional person.

The system 2000 can provide an apparatus for analysis comprising: a device containing convolutional processing logic encoded in a semiconductor chip comprising: evaluation logic trained to analyze pixels within an image of a person in a vehicle, wherein the analysis identifies a facial portion of the person; identification logic trained to identify one or more facial expressions based on the facial portion; classifying logic trained to classify the one or more facial expressions for cognitive response content; scoring logic trained to evaluate the cognitive response content to produce cognitive state information for the person; and interface logic that enables manipulation of the vehicle based on communication of the cognitive state information to a component of the vehicle.

The system 2000 can provide a processor-implemented method for analysis comprising: using a device containing convolutional processing logic encoded in a semiconductor chip to perform: analyzing pixels within an image of a person in a vehicle, wherein the analysis identifies a facial portion of the person; identifying one or more facial expressions based on the facial portion; classifying the one or more facial expressions for cognitive response content; evaluating the cognitive response content to produce cognitive state information for the person; and manipulating the vehicle based on communication of the cognitive state information to a component of the vehicle.

The system 2000 can include one or more video data collection machines 2020 linked to an analysis machine 2040 and a manipulation machine 2050 via a network 2010 or another computer network. The network can be wired or wireless, a computer network such as the Internet, and so on. Video data 2060 can be transferred to the analysis machine 2040 through the network 2010. The example video data collection machine 2020 shown comprises one or more processors 2024 coupled to a memory 2026 which can store and retrieve instructions, a display 2022, a camera 2028, and a microphone 2030. The camera 2028 can include a webcam, a video camera, a still camera, a thermal imager, a CCD device, a phone camera, a three-dimensional camera, a depth camera, a light field camera, multiple webcams used to show different views of a person, or any other type of image capture technique that can allow captured data to be used in an electronic system. The microphone can include any audio capture device that can enable captured audio data to be used by the electronic system. The memory 2026 can be used for storing instructions, video data on a plurality of people, audio data from the plurality of people, one or more classifiers, and so on. The display 2022 can be any electronic display, including but not limited to, a computer display, a laptop screen, a net-book screen, a tablet computer screen, a smartphone display, a mobile device display, a remote with a display, a television, a projector, or the like.

The analysis machine 2040 can include one or more processors 2044 coupled to a memory 2046 which can store and retrieve instructions, and can also include a display 2042. The analysis machine 2040 can receive the video data 2060 and can analyze pixels within an image of a person in a vehicle. The analysis can identify a facial portion of the person, a portion of a torso of the person, and so on. The analysis that identifies the facial portion or other portion of the person can be accomplished using one or more classifiers. The one or more classifiers can be stored within the analysis machine, loaded into the analysis machine, provided by a user of the analysis machine, and so on. The analysis machine 2040 can use video data received from the video data collection machine 2020 to produce feature data 2062. In some embodiments, the analysis machine 2040 receives video data from a plurality of video data collection machines, aggregates the video data, processes the video data or the aggregated video data, and so on.

The manipulation machine 2050 can include one or more processors 2054 coupled to a memory 2056 which can store and retrieve instructions and data, and can also include a display 2052. The manipulation of a vehicle based on manipulation communication data 2064 can occur on the manipulation machine 2050 or on a machine or platform different from the manipulation machine 2050. In embodiments, the manipulation of the vehicle based on the manipulation communication data occurs on the video data collection machine 2020 or on the analysis machine 2040. As shown in the system 2000, the manipulation machine 2050 can receive manipulation communication data 2064 via the network 2010, the Internet, or another network, from the video data collection machine 2020, from the analysis machine 2040, or from both. The manipulation of the vehicle, which can include alerts, warnings, displays, cognitive state indications, and so on, can include a visual rendering on a display or any other appropriate display format.

The system 2000 can include a computer program product embodied in a non-transitory computer readable medium for image analysis, the computer program product comprising: code for executing on a device containing a convolutional processing logic encoded in a semiconductor chip comprising: evaluation logic trained to analyze pixels within an image of a person in a vehicle, wherein the analysis identifies a facial portion of the person; identification logic trained to identify one or more facial expressions based on the facial portion; classifying logic trained to classify the one or more facial expressions for cognitive response content; scoring logic trained to evaluate the cognitive response content to produce cognitive state information for the person; and interface logic that enables manipulation of the vehicle based on communication of the cognitive state information to a component of the vehicle.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are limited to neither conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. An apparatus for analysis comprising:
 a device containing convolutional processing logic encoded in a semiconductor chip comprising:
  evaluation logic trained to analyze an image of a person in a vehicle, wherein the analysis identifies a facial portion of the person;
  identification logic trained to identify one or more facial expressions based on the facial portion;
  classifying logic trained to classify the one or more facial expressions for cognitive response content;
  scoring logic trained to evaluate the cognitive response content to produce cognitive state information for the person; and
  interface logic that enables manipulation of the vehicle based on communication of the cognitive state information to a component of the vehicle wherein the manipulation includes a locking out operation.

2. The apparatus of claim 1 further comprising categorization logic that updates a cognitive state profile of an individual associated with the facial portion.

3. The apparatus of claim 2 wherein the cognitive state profile summarizes the cognitive state information of the individual.

4. The apparatus of claim 3 wherein the cognitive state profile is based on cognitive state event temporal signatures.

5. The apparatus of claim 1 wherein an additional facial portion from an image of an additional person within the vehicle is evaluated, identified, classified, and scored to produce additional cognitive state information for the additional person.

6. The apparatus of claim 1 wherein the cognitive state information is used to communicate one or more of drowsiness, fatigue, distraction, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

7. The apparatus of claim 1 further comprising logic for augmenting the cognitive state information based on audio data collected from within the vehicle, wherein the audio data is collected contemporaneously with the image.

8. The apparatus of claim 7 wherein the audio data includes voice data.

9. The apparatus of claim 1 wherein the manipulation of the vehicle further includes a recommending a break for an occupant, a recommending a different route for the vehicle, a recommending how far to drive, a responding to traffic, or an adjusting of seats, mirrors, climate control, lighting, music, audio stimuli, or interior temperature, a brake activation, or a steering control.

10. The apparatus of claim 1 further comprising logic for tagging the cognitive state information with sensor data received from the vehicle.

11. The apparatus of claim 1 wherein the cognitive state information that was analyzed is based on intermittent occurrences of the facial portion within a series of images.

12. The apparatus of claim 1 wherein a series of images is supplied to the device and wherein the series of images is sourced from a video stream.

13. The apparatus of claim 12 further comprising tracking logic trained for tracking the facial portion and identifying that the facial portion is no longer within images from the video stream.

14. The apparatus of claim 13 wherein the tracking logic identifies that a face has left the images from the video stream.

15. The apparatus of claim 14 wherein the tracking logic identifies that the face has returned to the images from the video stream and associates information previously collected about the face from before the face left the video stream.

16. The apparatus of claim 1 wherein the cognitive response content includes facial expressions.

17. The apparatus of claim 1 wherein the classifying logic is further trained to identify a gender, age, or ethnicity for a face associated with the facial portion.

18. The apparatus of claim 17 wherein the gender, age, or ethnicity is provided with an associated probability.

19. The apparatus in claim 1 wherein the cognitive state information is used by a software application running on a processor coupled to the device.

20. The apparatus of claim 19 wherein the processor comprises a mesh processor.

21. The apparatus in claim 1 wherein the device sends one or more images to a web service for external classification based on the cognitive state information.

22. The apparatus in claim 1 wherein the device further performs smoothing of the cognitive state information.

23. The apparatus in claim 1 wherein the device further performs image correction for the image including one or more of lighting correction, contrast correction, near infrared lighting correction, or noise filtering.

24. The apparatus in claim 1 wherein physiological information is gleaned from a video containing the image.

25. The apparatus of claim 1 further comprising logic for augmenting the cognitive state information based on audio data collected from outside the vehicle, wherein the audio data is collected contemporaneously with the image.

26. The apparatus of claim 1 wherein the cognitive state information includes a reaction of the person to weather conditions.

27. A computer program product embodied in a non-transitory computer readable medium for image analysis, the computer program product comprising:
    code for executing on a device containing a convolutional processing logic encoded in a semiconductor chip comprising:
        evaluation logic trained to analyze an image of a person in a vehicle, wherein the analysis identifies a facial portion of the person;
        identification logic trained to identify one or more facial expressions based on the facial portion;
        classifying logic trained to classify the one or more facial expressions for cognitive response content;
        scoring logic trained to evaluate the cognitive response content to produce cognitive state information for the person; and
        interface logic that enables manipulation of the vehicle based on communication of the cognitive state information to a component of the vehicle wherein the manipulation includes a locking out operation.

28. A processor-implemented method for analysis comprising:
    using a device containing convolutional processing logic encoded in a semiconductor chip to perform:
        analyzing an image of a person in a vehicle, wherein the analysis identifies a facial portion of the person;
        identifying one or more facial expressions based on the facial portion;
        classifying the one or more facial expressions for cognitive response content;
        evaluating the cognitive response content to produce cognitive state information for the person; and
        manipulating the vehicle based on communication of the cognitive state information to a component of the vehicle wherein the manipulation includes a locking out operation.

* * * * *